United States Patent
De Bruin et al.

(10) Patent No.: US 9,460,400 B2
(45) Date of Patent: *Oct. 4, 2016

(54) EXPERT SYSTEM FOR DETERMINING PATIENT TREATMENT RESPONSE

(71) Applicant: Digital Medical Experts Inc., Waterloo, Ontario (CA)

(72) Inventors: Hubert De Bruin, Ancaster (CA); Gary Hasey, Toronto (CA); Ahmad Khodayari-Rostamabad, Hamilton (CA); Duncan Maccrimmon, Burlington (CA); James Reilly, Hamilton (CA)

(73) Assignee: Digital Medical Experts Inc. (CA)

( * ) Notice: Subject to any disclaimer, the term of this patent is extended or adjusted under 35 U.S.C. 154(b) by 305 days.

This patent is subject to a terminal disclaimer.

(21) Appl. No.: 14/182,269

(22) Filed: Feb. 17, 2014

(65) Prior Publication Data

US 2014/0279746 A1 Sep. 18, 2014

Related U.S. Application Data

(63) Continuation of application No. 12/918,810, filed as application No. PCT/CA2009/000195 on Feb. 20, 2009, now Pat. No. 8,655,817.

(51) Int. Cl.
G06F 15/18 (2006.01)
G06N 99/00 (2010.01)
(Continued)

(52) U.S. Cl.
CPC ............. *G06N 99/005* (2013.01); *A61B 5/00* (2013.01); *A61B 5/0476* (2013.01); *A61B 5/7267* (2013.01); *G06F 19/345* (2013.01); *G06N 5/02* (2013.01); *A61B 5/4088* (2013.01)

(58) Field of Classification Search
None
See application file for complete search history.

(56) References Cited

U.S. PATENT DOCUMENTS 5,860,917 A 1/1999 Comanor et al.
6,063,028 A 5/2000 Luciano
(Continued)

FOREIGN PATENT DOCUMENTS

WO 2006056024 A1 6/2006
WO 2006065763 6/2006

OTHER PUBLICATIONS

Ying Guo et al.; Predicting the brain response to treatment using a Bayesian hierarchical model with application to a study of schizophrenia; Human Brain Mapping; vol. 29 No. 9; Oct. 9, 2007; pp. 1092-1109.

(Continued)

*Primary Examiner* — Kakali Chaki
*Assistant Examiner* — Michael Zidanic
(74) *Attorney, Agent, or Firm* — Steven M. Greenberg; CRGO Law

(57) ABSTRACT

A medical digital expert system to predict a patient's response to a variety of treatments (using pre-treatment information) is described. The system utilizes data fusion, advanced signal/information processing and machine learning/inference methodologies and technologies to integrate and explore diverse sets of attributes, parameters and information that are available to select the optimal treatment choice for an individual or for a subset of individuals suffering from any illness or disease including psychiatric, mental or neurological disorders and illnesses. The methodology and system can also be used to determine or confirm medical diagnosis, estimate the level, index, severity or critical medical parameters of the illness or condition, or provide a list of likely diagnoses for an individual suffering/experiencing any illness, disorder or condition.

45 Claims, 14 Drawing Sheets

(51) Int. Cl.
*A61B 5/00* (2006.01)
*A61B 5/0476* (2006.01)
*G06F 19/00* (2011.01)
*G06N 5/02* (2006.01)

(56) References Cited

U.S. PATENT DOCUMENTS

| | | | |
|---|---|---|---|
| 6,463,321 | B2 | 10/2002 | Granger |
| 6,622,036 | B1 | 9/2003 | Suffin |
| 6,714,925 | B1 | 3/2004 | Barnhill et al. |
| 7,177,675 | B2 | 2/2007 | Suffin et al. |
| 7,231,245 | B2 | 6/2007 | Greenwald et al. |
| 7,444,308 | B2 | 10/2008 | Guyon et al. |
| 8,655,817 | B2 | 2/2014 | Hasey et al. |
| 2002/0143563 | A1 | 10/2002 | Hufford et al. |
| 2006/0047616 | A1 | 3/2006 | Cheng et al. |
| 2006/0064415 | A1 | 3/2006 | Guyon et al. |
| 2007/0288414 | A1* | 12/2007 | Barajas ............ G06N 7/00 706/46 |
| 2008/0233576 | A1 | 9/2008 | Weston et al. |
| 2010/0280403 | A1 | 11/2010 | Erdogmus et al. |

OTHER PUBLICATIONS

Pilih I A et al.; Using machine learning for outcome prediction of patients with severe head injury; Computer-based medical systems; 1997 proceedings; Tenth IEEE Symposium on Maribor, Slovenia; Jun. 11-13, 1997; Los Alamitos, CA, USA; IEEE Comput. Soc.; US; Jun. 11, 1997; pp. 200-204.

J. A. Sanandres-Ledesma et al.; A performance comparative analysis between rule-induction algorithms and clustering-based constructive rule-induction algorithms. Application to rheumatoid arthritis. In: Field programmable logic and application; Jan. 1, 2004; Springer Berlin Heidelberg; vol. 3337, pp. 224-234.

Burges C J C; Geometric methods for feature extraction and dimensional reduction; Data mining and knowledge discovery handbook: a complete guide for practitioners and researchers; Kluwer academic publishers; Jan. 1, 2005; pp. 1-34.

Frey B J et al.; A comparison of algorithms fpr inference and learning in probabilistic graphical models; IEEE transactions on pattern analysis and machine intelligence; IEEE service center; Los Alamitos, CA, US; vol. 27 No. 9; Sep. 1, 2005; pp. 1392-1416.

Smola A J et al.; A tutorial on support vector regression; Neurocolt technical support; Jan. 1, 1998; pp. 1-71.

Roweis S, Ghahramani Z, "A unifying review of linear Gaussian models," Neural Computation 1999, vol. 11, pp. 305-345.

Evgeniou T, et al., "Regularization networks and support vector machines," Advances in Computational Mathematics 2000, vol. 13, pp. 1-50.

Hastie T, et al., "The Elements of Statistical Learning: Data Mining, Inference, and Prediction," Springer Series in Statistics, Springer, Second Edition, 2003, pp. 11-16.

Rosipal R, et al., "Kernel partial least squares regression in reproducing kernel Hilbert space," Journal of Machine Research 2, 2001, vol. 2, pp. 97-123.

Torra V., "Information fusion in data mining", Studies in Fuzziness and Soft Computing, Springer, vol. 123, pp. 188-208, 2003.

Sinha A, et al., "Estimation and decision fusion: a survey", Proceedings IEEE Int. Conf. on Engineering of Intelligent Systems 2006, pp. 1-6.

Peng et al., Feature Selection Based on Mutual Information: Criteria of Max-Dependency, Max Relevance, and Min-Redundancy, IEEE Transactions on Pattern Analysis and Machine Intelligence, vol. 27, No. 8, pp. 1226-1238, 2005.

Connor, J.P. et al.; The Application of Machine Learning Techniques as an Adjunct to Clinical Decision Making in Alcohol Dependence Treatment; Substance Use & Misuse; vol. 42, pp. 2193-2206; 2007.

* cited by examiner

EXPERT SYSTEM FOR DETERMINING PATIENT TREATMENT RESPONSE

CROSS-REFERENCE TO RELATED APPLICATIONS

This application is a Continuation of U.S. application Ser. No. 12/918,810, filed Jan. 31, 2011, entitled "EXPERT SYSTEM FOR DETERMINING PATIENT TREATMENT RESPONSE," which was a Submission Under 35 U.S.C. §371 for U.S. National Stage Patent Application of International Application Number PCT/CA2009/00195, filed Feb. 20, 2009, and entitled "EXPERT SYSTEM FOR DETERMINING PATIENT TREATMENT RESPONSE," and is related to U.S. Provisional Application No. 61/064,177 filed on Feb. 20, 2008, the entirety of which are incorporated herein by reference.

BACKGROUND OF THE INVENTION

The present invention relates to the field of medical treatments and, more specifically, to predicting treatment efficacy and determining optimal treatment for any illness, disease or abnormality including psychiatric and neurological disorders. It also relates to the field of medical and clinical cognitive systems and methods of performing medical diagnosis and estimating and assessing the type, severity, level or critical medical/clinical parameters of any illness, disease, disorder or condition.

Major depressive disorder (MDD) is a serious mental disorder and is now the third largest cause of workplace disability. It has been estimated that by the year 2020, depression may account for 15% of total global disease burden, second only to ischemic heart disease.

Despite the severity of MDD, the procedure for selecting optimal treatment is not well developed. The choice of antidepressant therapy is currently based on personal preference, weighted by clinical factors such as family history, symptom clustering and previous medication history. However, it is not uncommon for the first medication used to prove ineffective and the increasingly despondent patient is subjected to a series of medication trials before one that works is found. Since an adequate antidepressant trial should be of at least 4 to 6 weeks duration, the personal and economic cost of delayed or ineffective therapy is substantial. Clearly, a method of reliably choosing an effective treatment before the initial trial would be of immense clinical and economic value.

Moreover, although patients may appear to have similar clinical characteristics, a treatment that works for one patient, may not work well for others. This suggests that current diagnostic systems and testing procedures may not be sufficiently sensitive to detect subtle but highly relevant differences between patients presenting with similar complaints.

It is also difficult to make full use of the test data provided using current technologies. The wide array of psychological, physical, hematological, radiological and other laboratory tests generate a very large information set that the busy clinician may find challenging to compile and process. The vast amounts of data that may be generated are typically viewed in isolation or as part of simple syndromatic clusterings. It is possible that a great deal of salience with respect to diagnosis and treatment that is embedded in these data may not be extracted using these basic analytic methods. The abundance and complexity of this information requires a new approach to data management and analysis methods to assist the physician/clinician to make diagnosis and treatment decisions with greater accuracy and efficiency.

For example, mental and neurological illnesses such as mood disorders, schizophrenia, anxiety disorders, epilepsy, Parkinson's disease and dementias of Alzheimer's and other types are common and debilitating conditions for which current treatment algorithms lack precision. The process for assessing an effective therapy (specifically, medication therapy) is poorly defined at best. In short, the basic procedure is to prescribe a therapy on a trial and error basis until one is found that is effective.

Furthermore patients must often wait lengthy periods of time before seeing the clinical experts who possess the skill to effectively treat these conditions, particularly in rural areas where such specialists are few in number. As a result family physicians are often obliged to initiate treatment themselves without the benefit of the extensive experience and knowledge possessed by psychiatrists and neurologists. Even among the clinical experts it is acknowledged that patients meeting the diagnostic criteria for most psychiatric and neurological conditions are not uniformly responsive to the same treatment. Some patients respond well to a given treatment while others, with very similar clinical features, do not.

Treatment failure may be a function of extraneous factors such as treatment adequacy (in terms of medication dose and duration of treatment), poor absorption of oral medication, unusual medication metabolism or inadequate patient adherence to prescribed treatment. However, individual patients often fail to respond to a particular treatment whose efficacy has been demonstrated in large clinical trials. This suggests that biological subtypes may exist within a given syndrome or diagnostic category. Patients afflicted with a particular biological subtype of a condition or diagnosis may respond preferentially to only some of the many medication treatments available to treat that condition or diagnosis. Often, even expert clinicians cannot readily distinguish these illness subtypes using current methodology. This suggests that current diagnostic systems and testing procedures may not be efficiently exploring the information to detect subtle but highly relevant differences between patients presenting with similar complaints.

This phenomenon is readily apparent for patients with major depressive disorder (MDD) treated with antidepressant medications. For the first trial of antidepressant medications the remission rate may be as low as 28%. While up to 67% of patients with MDD will eventually respond, this may require several different antidepressant drug trials, each of several weeks duration. Similar problems determining optimal treatment apply to other psychiatric illnesses such as bipolar disorder, postnatal depression and schizophrenia or neurological conditions such as Parkinson's disease, epilepsy, stroke, brain tumor, Alzheimer's disease and other forms of dementia.

The first step in determining efficient treatment is establishing a correct diagnosis. This can be a more difficult task than it might seem. Specific symptoms can appear in more than one diagnostic category and diagnostic criteria can overlap to the point where confident differentiation of one condition from another is impossible. For example, though clinical acumen has been evolving over generations, selection of optimal antidepressant treatment on the basis of a standard psychiatric assessment remains an elusive objective.

Several attempts have been made to develop improved methods of determining effective treatment. For example, U.S. Pat. No. 7,177,675 and US Patent Application 2008/

0125669 describe a method and system for utilizing neurophysiologic information obtained by techniques such as quantitative electroencephalography (QEEG, or EEG) and magnetoencephalography (MEG) in appropriately matching patients with therapeutic entities. In particular, methods for comparing neurophysiologic information relative to a reference set are disclosed along with database-based tools for deducing therapeutic entity actions on particular patients such that these tools are accessible to remote users. However, U.S. Pat. No. 7,177,675 merely discloses simple mathematical techniques that do not efficiently capture the complexity inherent in the data and in the problem and do not have flexibility in computational and modeling structure. Furthermore, this patent emphasizes that prediction of treatment response is best done using EEG data alone without any reference to diagnosis or symptomatic presentation. Although it is acknowledged that current diagnostic systems do not explain all of the variance in treatment response seen in clinical practice, removing diagnosis as the fundamental staring point of treatment planning disregards extensive research evidence and clinical experience indicating that symptomatic features, family history, personality, psychological attributes, social context and other clinical features can be useful in predicting treatment response. Although an extensive list of medication therapies are specifically mentioned in the patent, this list does not include prediction of response to repetitive transcranial magnetic stimulation (rTMS or TMS) therapy.

The method claimed in U.S. Pat. No. 7,177,675 is not inherently adaptive and self-improving.

U.S. Pat. No. 7,231,245 describes a system and method that assesses neurological conditions and predicts responsiveness to medication using some linearly defined features and indices. This patent also describes a system and method that produces features and indices that indicate the presence or absence of a disease or condition, or of the progression of a disease or condition. Such features and indices are derived from electroencephalography (EEG) variables obtained from time domain, power spectrum, bispectrum and higher order spectrum values that are derived from biopotential signals taken from the subject being tested. This patent describes a "differential testing methodology" comprising an infusion device capable of administering a controlled dose of a pharmacological agent. The EEG signal changes induced by the drug infused are then examined.

There remains however, an unmet need for a method with improved accuracy and efficiency of the prediction and estimation models. Thus, it is an objective of the present invention to propose a solution which resolves or at least alleviates one or more of the problems identified above.

SUMMARY OF THE INVENTION

Thus, in accordance with the present invention, there is provided a method for assessment of status of a patient (for diagnosis, treatment selection, treatment efficacy prediction, severity assessment, disease progression or otherwise), the method comprising:

generating a first level training dataset comprising a plurality of records comprising patient related clinical, symptomatic and laboratory data from a large number of patients on a system database;

processing the first level training dataset in a series of processes including preprocessing, feature extraction, and dimensionality reduction processes to select a reduced-dimension feature data subset. The reduced feature data subset being derived by means of processing the data to compute features appearing to be discriminative and relevant for a useful assessment of the patient status;

processing the reduced feature data to derive a data processor scheme or model relating feature data and an assessment status. The processor/model performs the modeling and analysis tasks including classification, regression, estimation, prediction, and detection. A collection of various preliminary processors/models is used in parallel, and the data fusion procedure combines these preliminary processors to find the final optimal results. Fusing the results of several processors/models provides better performance than an individual processor/model;

generating and collecting treatment-planning and diagnosis datasets including the features derived for the related feature data subset and the corresponding target values, such as reference diagnosis values, true values of attribute of interest, or treatment outcomes;

using the treatment-planning and diagnosis datasets in a learning or training procedure to construct the processors and models and find their unknown parameters which are used for assessment of the patient, medical/clinical diagnosis and treatment planning models.

In one realization, the invention provides a method for predicting patient response, in which the method comprises generating, and storing on a system database, a first level training dataset comprising a plurality of records comprising measured patient related clinical and/or laboratory data feature information from a large number of patients, the data including data relating to patient treatment response; wherein the measured patient related clinical and/or laboratory data is processed to extract features from the measured data;

processing the extracted feature dataset to select a reduced feature data subset whose cardinality is less than that of the first level training data set containing the clinical and/or laboratory data features; the reduced feature data subset being derived by means of processing the data to select features appearing to discriminate for a useful prediction;

processing the reduced feature data to derive a feature data scheme or model relating feature data and treatment response;

generating a subject patient dataset including the features selected for the reduced feature data subset;

comparing the subject patient dataset to the feature data scheme or model to predict a response for the patient.

In accordance with one aspect of the invention, there are two steps to acquiring a set of reduced features: 1) the "raw" measured patient related clinical and/or laboratory data is processed to obtain a set of $N_c$ first-level features. These can be statistical quantities, can be transformed variables (e.g. Fourier coefficients at specific frequencies), and other types of coefficients that need some processing to extract. This step may be referred to as "feature extraction". 2) the next step is to reduce the $N_c$ first-level features to a smaller set containing only $N_i$ reduced features where $N_c \gg N_i$. This step may be referred to as called feature reduction, feature compression, feature selection or dimensionality reduction.

The feature reduction process can be visualized as a processing box where all $N_c$ features are input, and only $N_i$ are output. Each output can be a different function of all the inputs; the number (cardinality) $N_i$ of outputs is smaller than the number of inputs. This is more general than simply deleting some and keeping the others unmodified.

In an alternative aspect, the invention provides a medical/clinical system comprising:

training databases holding or comprising a multiplicity of patient data records, in which each patient data record includes a multiplicity of clinical, symptomatic and laboratory data and includes the corresponding outcome data relating to patient assessment status (for diagnosis, treatment selection, severity assessment, disease progression or otherwise);

means for processing the clinical, symptomatic and laboratory data of a patient using the medical/clinical diagnosis models/schemes and treatment-planning models, and reporting back the outcome. The models and processors are built based on the information in the training datasets in a process called learning/training or adaptation.

Beneficially the treatment-planning, treatment efficacy prediction and diagnosis model or processor allocates feature data values to a treatment response category (or other assessment status when doing diagnosis).

It is preferred that the feature data scheme model or processor is built by means of solving a numerical optimization problem based on optimality criteria which are constrained to the structure of the model as well as to the information in the training datasets. One optimality criterion is defining functions to segregate or discriminate between response (or other assessment status) categories based on the minimizing the 'regularized model error' which is a trade-off between minimizing the model complexity and minimizing the modeling error. In one embodiment, the models are built based on defining non-linear discrimination boundaries between feature data values of different types in high-dimensional feature-space. In another embodiment based on statistical models, the optimality criteria includes one of the followings or their combination: minimizing the probability of modeling error, minimizing the probability of modeling cost, maximizing the likelihood, minimizing the modeling complexity as well as minimizing the modeling error. Many models operate in parallel and the outcomes are combined in a data fusion procedure to obtain the final result which provides a higher efficiency than using a single model.

Different techniques may be used to achieve an effective result. The feature data scheme or model may be determined by evaluating any form of probability of the reduced input feature data values and determining the output class according to a maximum probability. A probabilistic graphical procedure may be used.

The feature data scheme or model may be determined by a Bayesian learning or decision technique.

The feature data scheme or model may be determined by fitting a mathematical function or model to the reduced feature training data by minimizing an error criterion.

The feature data scheme or model may be determined using information theoretic methods.

The feature data scheme or model may be determined using an artificial neural network.

The feature data scheme or model may be determined using methods based on artificial intelligence.

The feature data scheme or model may be determined using a mixture of factor analysis (MFA) technique.

The feature data scheme or model may be determined using a combination of these methods.

The feature data scheme or model may be determined using a parallel bank of independent classifiers, operating on the same reduced input feature data. The output values from each classifier are fed into a second-level processor structure where the output values are combined with the benefit of a training process to produce a single refined output value.

It is preferred that the data processors and computational models are built by means of processing the measured information according to a criterion of optimality as well as exploration of the training databases. The models are constructed according to one or more criteria based on one or more statistical methods, Bayesian methods, regularization methods, pattern recognition methods, least pth methods (where p is a real number greater than 0), geometric techniques, methods based on artificial intelligence, fuzzy logic or knowledge based systems, or on information theoretic approaches.

In one realization, it is preferred that one or more of the clinical data are derived by means of a brain activity or brain structure monitoring system, such as an electromagnetic monitoring system.

The expert prediction system of the present invention is based on a machine learning methodology. The neuro-psycho-biological information obtained from the patient before starting the treatment, before treatment planning or before making clinical/medical diagnosis makes a multidimensional observation vector. For example, in experiments conducted during the development of the invention (these experiments being discussed in detail hereinafter), pre-treatment EEG signals and clinical attributes are collected. The EEG data includes the signals collected by many sensors placed on the scalp, which are then pre-processed to obtain some meaningful raw features that might be relevant to predict the treatment efficacy. These raw features are then compressed in an optimal or sub-optimal manner to produce a set of reduced or compressed features. These compressed features are then fed into a classifier or regressor which outputs a desired value corresponding to the "status" of the patient. The status can include predicted response to a treatment, a diagnosis, an indication of disease progression, a susceptibility to an illness, or other items of medical interest.

The classification process may be viewed as a mapping $f(x_i): R^{N_i} \rightarrow N$ from a point $x_i$ in an input feature space (to be defined later) into a discrete output space which corresponds to the respective classes of the input. The second aspect of machine learning is the regression problem where the function $f(\bullet)$ is continuous; i.e., $f(\bullet) \in R$. In this case, $f$ gives an estimate of the parameter(s) of interest. It is to be noted that regression can also be used for classification, in that the regression output can be discretized into a discrete variable corresponding to the class. Thus for our purposes, we consider regression and classification to be equivalent processes and providing a means for establishing a model, scheme or processor relating feature data to corresponding treatment outcome or response (or other assessment status, or diagnosis).

The first step in a machine learning procedure is to transform the observed data into a discriminative feature space. The extraction of relevant features/attributes is always a critical issue in any machine learning application. Effective features depend greatly on the underlying problem, but typically they include an assortment of various attributes characterizing statistical, geometrical, temporal, hierarchical and dynamic model properties of the measured data. The number $N_c$ of candidate features can therefore become very large. For optimum performance of the prediction/classification algorithm, it is necessary to reduce the dimensionality of the feature and to transform the candidate set containing $N_c$ features into a subset containing only $N_i$ features, where $N_i \leq N_c$.

The $N_i$ features are extracted from the observed data and assembled into a vector $x_i \in R^{N_i}$. The associated class, treatment responsiveness label or target value (assumed known) corresponding to the observed data sample i (of a patient) is denoted by the variable $y_i \in N$ (classification) or $y_i \in R$ (regression). The set $D_t = \{(x_i, y_i), i=1, \ldots, M_t\}$ is referred to as the training set, where $M_t$ is the number of training samples available. Given a set of training patterns, the objective is to determine the function $f$. For classification, $f$ establishes decision boundaries in the feature space which effectively separate patterns belonging to different classes. For regression, $f$ is determined to give as close a fit as possible to the values $y_i$ corresponding to the input feature vector $x_i$.

If $N_i$ is relatively large compared to $M_t$, then numerical stability and over—training issues can arise, with the result that the estimated function $f$ has large variance. If $N_i$ is too small relative to $N_c$, then the selected features may not adequately describe the clustering behaviour of the observations. Both of these scenarios lead to poor performance.

Therefore, it is apparent that only those features which provide the best discriminating power for the classifier/predictor should be retained. The choice of these features is an interesting problem and is discussed in greater detail hereinafter.

The function $f$ is determined through a training process with the use of training data. The data model is assumed to be of the form $$y_i = f(x_i; \Theta) + n_i, i=1, \ldots, M_t$$

where $n_i$ are independent additive random variables, (modeling measurement noise, etc), whose probability distribution is unknown. The variable $\Theta$ represents the parameters of the model function $f$ which are to be determined.

There are many methods of determining the function $f$. The determination of $f$ is, in essence, equivalent to the design of the classifier/regressor/predictor. Classifier structures include the support vector machine, Bayesian classifiers, regularized least squares, fuzzy networks, Bayesian networks and many more. For example, geometric classifiers work on the principle of specifying a hyperplane or nonlinear boundaries in an $N_i$-dimensional space to optimally separate the clusters corresponding to the classes, so that the probability of a mis-classification as well as the complexity of the classification model is minimized. One type of methods of interest in relation to the present invention are based on the general principle of measuring the expected discrepancy between the target y and $f(x_i; \Theta)$ for a given input $x_i$, by some loss functional L (y, $f(x;\Theta)$), which is based on 'the regularization theory' in which a 'trade-off' is made between minimizing the modeling error and minimizing the complexity of the model.

BRIEF DESCRIPTION OF THE DRAWINGS

These and other aspects of the present invention will be apparent from, and elucidated with reference to, the embodiment described herein.

An embodiment of the present invention will now be described by way of example only and with reference to the accompanying drawings, in which:

FIG. 10.a shows projection of data samples or epochs, and FIG. 10.b shows a subject-wise scatter plot of projected pre-treatment data in SSRI therapy.

FIG. 12.a shows epochs or data samples, and FIG. 12.b shows a subject-wise scatter plot of projected data. 'R' corresponds to TR<88.5, and 'NR' corresponds to TR>−88.5.

FIG. 14.a shows normal subjects versus patients with MDD or schizophrenia, and FIG. 14.b shows MDD versus schizophrenic patients.

DETAILED DESCRIPTION OF THE PREFERRED EMBODIMENTS

The present invention provides a "medical digital expert system", that is a computer-based mathematical method capable of analyzing neurophysiological information plus a wide range of clinical and laboratory data to predict treatment outcome/efficacy and, optionally, to estimate diagnosis. Alternatively, the methodology and system can be called a "digital clinician", or a "cognitive medical expert system", playing the role of an expert physician/clinician that extensively processes/analyzes the available clinical and laboratory information of a patient, to facilitate a medical diagnosis or make treatment recommendations. The system can provide an estimation of the level, severity, or critical medical attributes of a condition, and/or the best treatment options.

Figure 1:
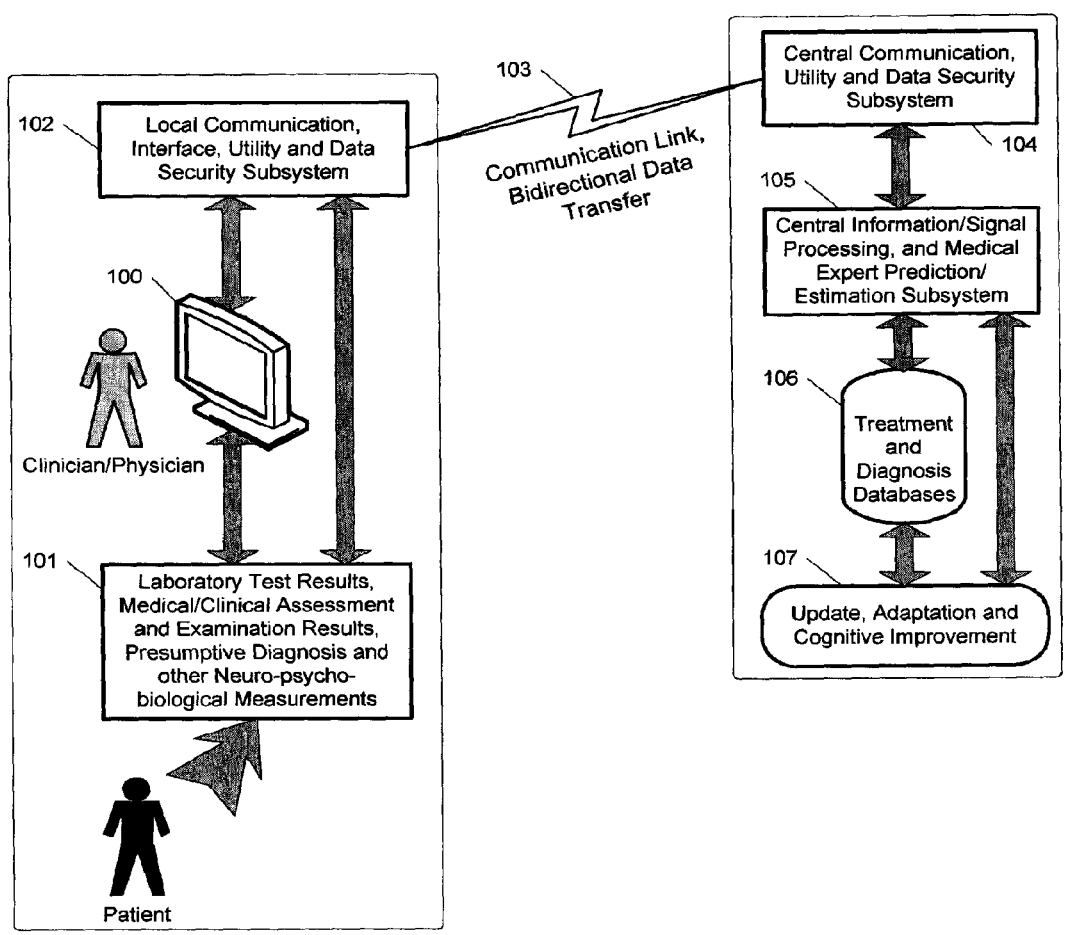
FIG. 1 illustrates schematically one embodiment of a system with remote or central data/signal processing according to the present invention.

As shown in FIG. 1, in one embodiment, the "medical digital expert system" operates in the following manner. The physician, or an assistant, collects as much relevant biometric, demographic, neurological, psychological, psychiatric, laboratory and clinical information (101) as possible regarding the patient. This information could include an array of neuro-psycho-biological indicators such as demographic information, past history, symptomatic presentation, a list of medical co-morbidities, results of laboratory testing, selected measures of personality and cognitive functioning, pharmacogenetic data, and biological data derived from electrophysiological, magnetic, electromagnetic, radiological, optical, infra-red, ultrasonic, acoustic, biochemical, medical imaging and other investigative procedures and attributes. The physician's presumptive diagnosis is also provided if available. This data is then either processed on-site using a computer algorithm pre-loaded into the user's computer or similar digital processing device, or sent electronically (103) to a remote central processing site. In both instances the data will be analyzed according to a machine learning and inference process (104-106). This process will generate a report consisting of the response-probabilities associated with a range of possible treatments for the condition diagnosed, and optionally, a list of diagnostic possibilities rank-ordered by likelihood. The list of recommended treatments with associated response probabilities, and optionally, a list of diagnostic possibilities rank-ordered by probability or likelihood, is then sent to the physician in a timely fashion (100-103).

For mental and neurological illnesses and disorders, measures of brain and nervous system functioning and anatomy such as EEG waveforms, the magnetic resonance imaging (MRI) scans, various other medical imaging, and various clinical and laboratory assessments can generate a large set of quantitative values/information. Efficient analysis of this highly complex dataset is beyond the capacity of the average human being, even one skilled in the art. The present invention provides an intelligent methodology to accomplish this difficult task by employing computational devices and advanced cognitive signal/information processing procedures. This analytic method allows the user to (optionally) estimate diagnosis and to subdivide patients meeting diagnostic criteria for a particular illness into subgroups with preferential response to a particular form or forms of treatment. The present method eliminates much of the uncertainty inherent in current clinical practice and represents a significant advance in clinical management.

The system and methodology of the present invention is based on advanced "signal/information processing" and "machine learning and inference" techniques. This invention includes a digital automated medical expert system capable of integrating diverse sets of neurological, psychological, psychiatric, biological, demographic and other clinical data to enhance the effectiveness of the physician by using machine learning and inference methods to estimate the probability of response to a range of treatment possibilities appropriate for the illness diagnosed, and, optionally, to provide a list of diagnostic possibilities rank-ordered by likelihood/probability. The signal/information processing method includes several stages including pre-processing, filtering, feature extraction and feature selection, low-dimensional representation, data clustering, statistical and Bayesian modeling and analysis, geometrical analysis, decision/estimation networks, building and learning predictive and estimator models using training data, and incorporating established and tested treatment guidelines and diagnostic classification systems. The rules and models will be improved by learning, combining and fusing different machine learning methods to build a hierarchical, multi-level and structured system and model that processes and compiles the data in different levels and handles missed attributes.

Figure 5:
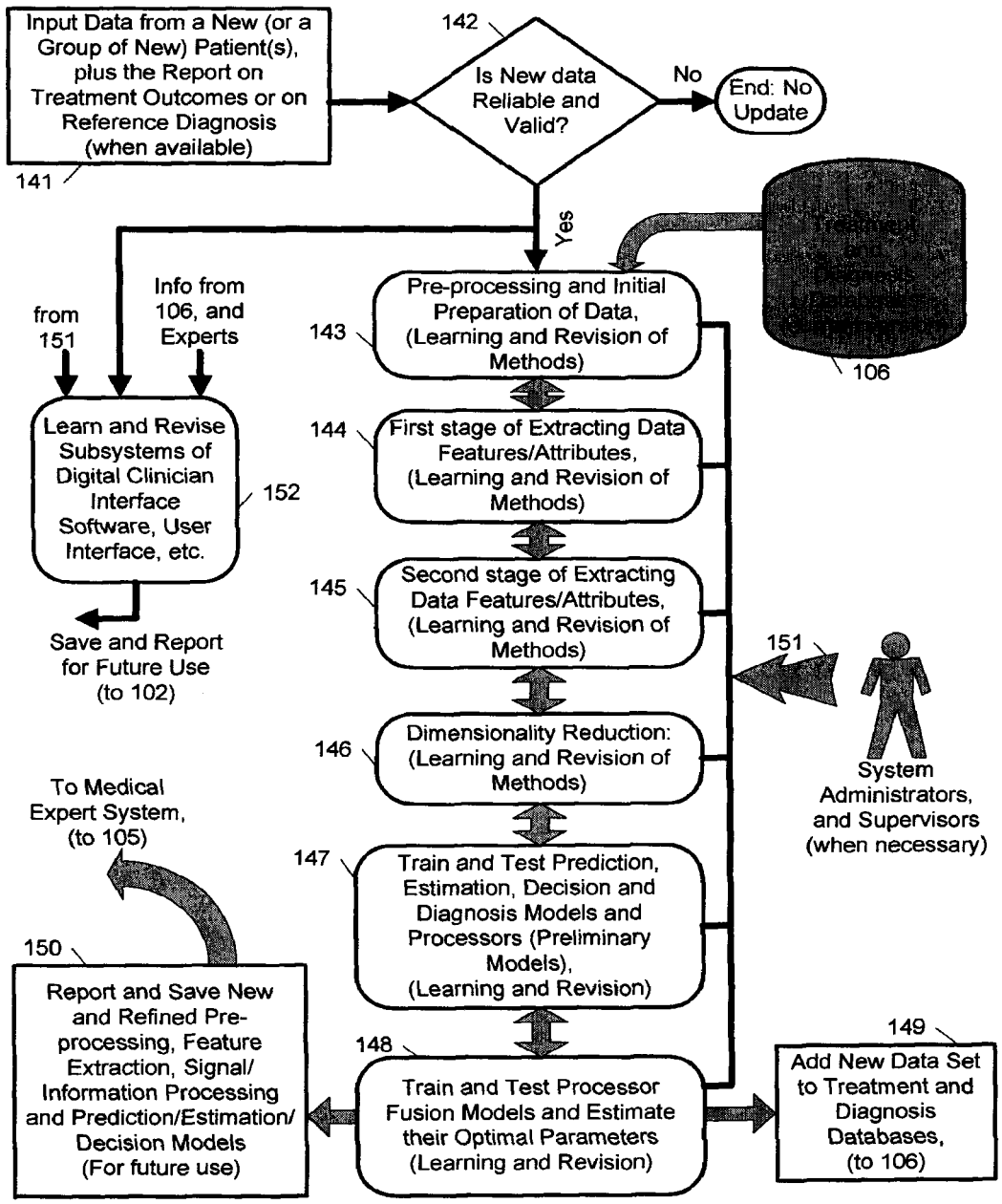
FIG. 5 is a flow chart illustrating a gradual and adaptive update and improvement process in accordance with one embodiment of the invention.
Figure 6:
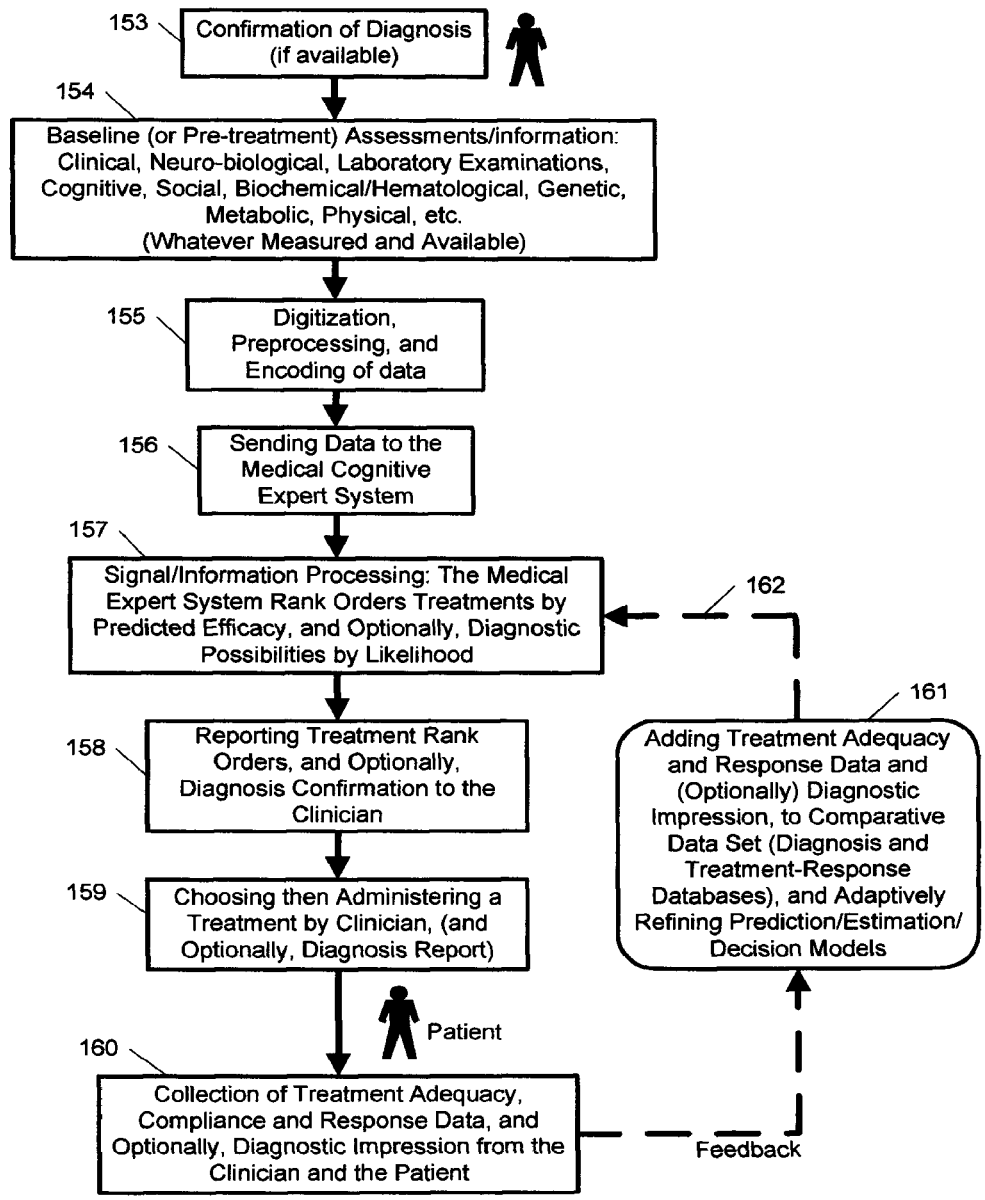
FIG. 6 illustrates one embodiment of a treatment selection, and optional diagnosis confirmation process in accordance with the invention.

A key component of the "medical digital expert system" is an adaptive or gradual learning capability (107). The performance of any classification/recognition or regression process depends heavily on the quantity and quality of the training data. In this invention, the system improves its own performance and reliability through continually acquiring new training data as it becomes available. This is accomplished by feedback from the family physician, clinician and/or patient to the central processing site. This feedback consists of both qualitative and quantitative data describing the patient's response to the prescribed treatment interpreted within the context of an estimate of the patient's reliability as a historian, adherence to treatment and adequacy of prescribed therapy (e.g. drug dose and duration of administration). Only outcome data collected from a reliable historian after an adequate course of treatment is added to the training dataset, and used to improve the performance of the classification/recognition algorithm by enhancing the computational methods and system for treatment-response-prediction. Optionally, further data regarding the accuracy of the initial diagnosis as offered by the disclosed diagnostic estimation/detection/prediction algorithm will be collected from the patient's clinician who, by this time, will have made further observations of the patient including review of new laboratory data and assessment of the effectiveness of the treatment prescribed. As shown in FIG. 5, only reliable and valid data are added to the estimation/prediction models. A report indicating the likelihood of response to a range of treatments/therapies appropriate for the condition diagnosed, and optionally a range of diagnostic possibilities, is returned in a timely manner to the clinician. Although this system can use the physician's estimated diagnosis (when available), findings suggestive of an alternate diagnosis to the one preferred by the physician can be identified and this information conveyed to the attending physician.

While this system may be useful to the family practitioner as well as the expert specialist physician, it will be of particular utility in circumstances where expert specialists or family physicians may not be readily available, and care must be administered by other clinically trained personnel such as nurse practitioners or other non-physician providers. In various embodiments, applications and examples, the user of the medical digital expert system can be a physician, a clinician, an assistant, a nurse, a patient who has access to relevant attributes and information about himself/herself, a laboratory operator, a health professional, a researcher or an organization seeking to screen out individuals who may be at risk of developing a psychiatric, neurological or medical illness or condition.

As an example description of the problem, there are many potential "indicators" of patient response to treatment in the case of psychiatric illnesses and disorders. These include various features obtained from the EEG, functional magnetic resonance imaging (fMRI), personality traits, economic and social status, previous psychiatric history, sleep patterns, etc. For example, subjects with higher metabolic rates in certain regions of the brain, as indicated by fMRI images, may respond better to anti-depressant medications such as venlafaxine. Also, patients with abnormal sleep EEG profiles are reported to have significantly poorer clinical response to short-term interpersonal psychotherapy.

Machine learning paradigms, otherwise known as cognitive data/information processing, pattern classification or pattern recognition and regression methods, artificial or computational intelligence, data mining, statistical data analysis, computational learning, and cognitive machines, etc., are capable of sorting objects into classes in the way a human can. Such methods can, for example, determine whether a particular image best represents either a "nut" or a "bolt". These algorithms extract "features" or attributes from the image. The features are designed so that they cluster according to the class of the object over specific regions in Euclidean space. An important aspect of any machine learning procedure is the acquisition of training data. Training data consist of objects presented to the classifier whose classes are known. This enables the classifier to identify the characteristics, models and clusters according to class. In one simple method of this kind, for example, when an object whose class is unknown is presented to the classifier, its class can be determined by finding the cluster which most closely corresponds to the features extracted from the object. Machine learning can also be used to construct models that do regression or interpolation, where the target variable is continuous.

In the past, the indicators discussed above have been used in isolation to predict the response or lack thereof to a particular treatment. The method of the present invention combines the information from as many indicators/attributes as possible into a machine learning process which classifies the predicted patient diagnosis and/or response to a set of given treatments. The use of a wide assortment of features significantly improves the quality of the prediction in comparison to previous methods.

In one embodiment of the present invention, the present system works as a digital version of an experienced clinical expert (expert physician, psychiatrist or neurologist, for example) who reviews various available information including neuro-psycho-biological, clinical, laboratory, physical, and pharmacogenetic data and information and evidence to confirm the diagnosis, to estimate a number of diagnostic possibilities and to rank order, by likelihood of response, a number of treatment options that might be reasonably considered to treat that illness or condition.

Ideally, the predictive accuracy of the medical digital expert system is optimal when the available neuro-psycho-biological data for a given test patient is maximized. However, in practice, because of time, cost, accessibility or other factors, patients do not receive every possible investigation and test. Therefore the disclosed system is designed to flexibly operate with incomplete data, provided that required minimum data requirements have been met (e.g. age, sex and EEG data in psychiatric illnesses and disorders). The set of available data and attributes for each patient is analyzed by the expert system, and the treatment response prediction, and optionally, the diagnostic estimation result, will be sent to the physician in electronic format. As an example, for a suspected mood disorder, in one of its simplest routines, a set of EEG data and a selected set of clinical depression rating scales are recorded and entered into the medical digital expert system. However, measuring more clinical and laboratory data and collecting more laboratory data, neuro-biological, psychological, personality and cognitive attributes and information may assist the expert system and will increase its performance, by reducing the ambiguities and extracting relevant and critical information that are hidden in various forms of data. In another embodiment, the disclosed system would send a prompt to the clinician requesting the results of a particular test, procedure or other clinical information that could significantly improve the performance of the algorithm. This new data could be then included in a reanalysis.

Some preferred embodiments are illustrated in the attached Figures. The prediction methodology involves three steps as illustrated in FIGS. 1, 2, 3 and 6. The first is the data acquisition step, in which neurophysiologic parameters that may include, but are not limited to, clinical and laboratory data are collected (101, 154 and FIG. 3), and then sent to the central processing system (103 and 156). The second step involves processing the signals and producing prediction results and confidence measures (105 and 157), which are then sent back to the physician treating the patient (158). The third step involves an adaptation or learning facility so that performance can be steadily improved (See 107 in FIG. 5). This involves the use of feedback from the physician's office to the central processing system that indicates the response of the patient to the prescribed treatment, and optionally, the diagnostic impression of the clinician (141 and 160). The physician will provide an estimate of the reliability of the patient's self-assessment and reporting as well as the level of compliance of the patient with the treatment protocol. This information is then used to decide whether the patient's outcome measure(s) can be used to update the expert system (142). Valid response data along with the original neurophysiologic information can then be used as additional training data to enhance the performance of the system (161 and FIG. 5). In the present invention, advanced signal processing and expert decision and machine learning and inference methods are included in a data fusion structure. The current invention uses improved discriminative feature extraction and feature selection techniques. For each patient, it uses the available neuro-psycho-biological information and makes the treatment response prediction to a variety of therapies and, optionally, makes a rank-ordered estimate of diagnosis. The current invention uses statistical, dynamic, geometrical and hierarchical decision-making techniques, and a data fusion expert system, by which it optimally combines the preliminary results from these methods and calculates an overall final decision with confidence measures. Using more advanced machine learning methods and employing data fusion strategy provides improved estimation/prediction efficiency. For example, for psychiatric disorders, beyond what can be inferred using EEG measurement alone, this invention also uses presumptive diagnosis, personality, clinical and laboratory information, mood induction, stimulus driven, event-related and evoked potentials and other neuro-psycho-biological information acquisition, to determine the treatment-efficacy estimation/prediction, recommending the list of proper therapies with response likelihoods, and, optionally, a rank-ordered list of diagnostic possibilities. Using more extensive information increases the prediction/estimation performance. The present invention provides an adaptive and intelligent feedback system to assess predictive accuracy and improve performance and reliability through the addition of new pre-treatment neuro-psycho-biological data and post-treatment outcome information as this new data becomes available over time. As discussed earlier, to prevent degradation of training data validity, only data passing validity screens can be entered to increase the size of the training data set. As the training data set is enlarged, the present invention will acquire the capacity to predict response, and optionally, perform medical diagnosis, in a more diverse set of illnesses, diseases, disorders, and conditions and relate it to a more diverse set of therapies and treatments including repetitive transcranial magnetic stimulation (rTMS therapy), cognitive behavioral therapy (CBT), deep brain stimulation (DBS) therapy and other treatments. The invented method and system illustrates the idea of a "digital clinician" which uses and explores all information and experience that an expert clinician uses to do medical diagnosis and then provides a list of treatments that are most likely to be effective.

The medical expert system includes the following elements/subsystems:

(i) One element is the interface, data acquisition and communication software and hardware subsystem. Through this interaction medium, the clinician/physician or the clinician's assistant collects and records the relevant neuro-psycho-biological information. For example, it may include using a number of on-line diagnostic checklists, laboratory test templates, clinical rating scales, interview forms and questionnaires to be completed by the patient or a rater before treatment is initiated (see 100, 101, and 102). The results of the routine laboratory testing and neuro-biological information derived from such tests as EEG, magnetoencephaolography (MEG), MRI and fMRI are analyzed on-site (110), or sent to a remote site for processing (through 102 and 103), and the list of treatment options with associated response probabilities, and optionally, a rank-ordered estimate of diagnosis will be sent to the physician/clinician. As mentioned, the expert system does not require measurement of all the aforementioned features/attributes and information and it will function with a subset of the aforementioned features/attributes.

Figure 7:
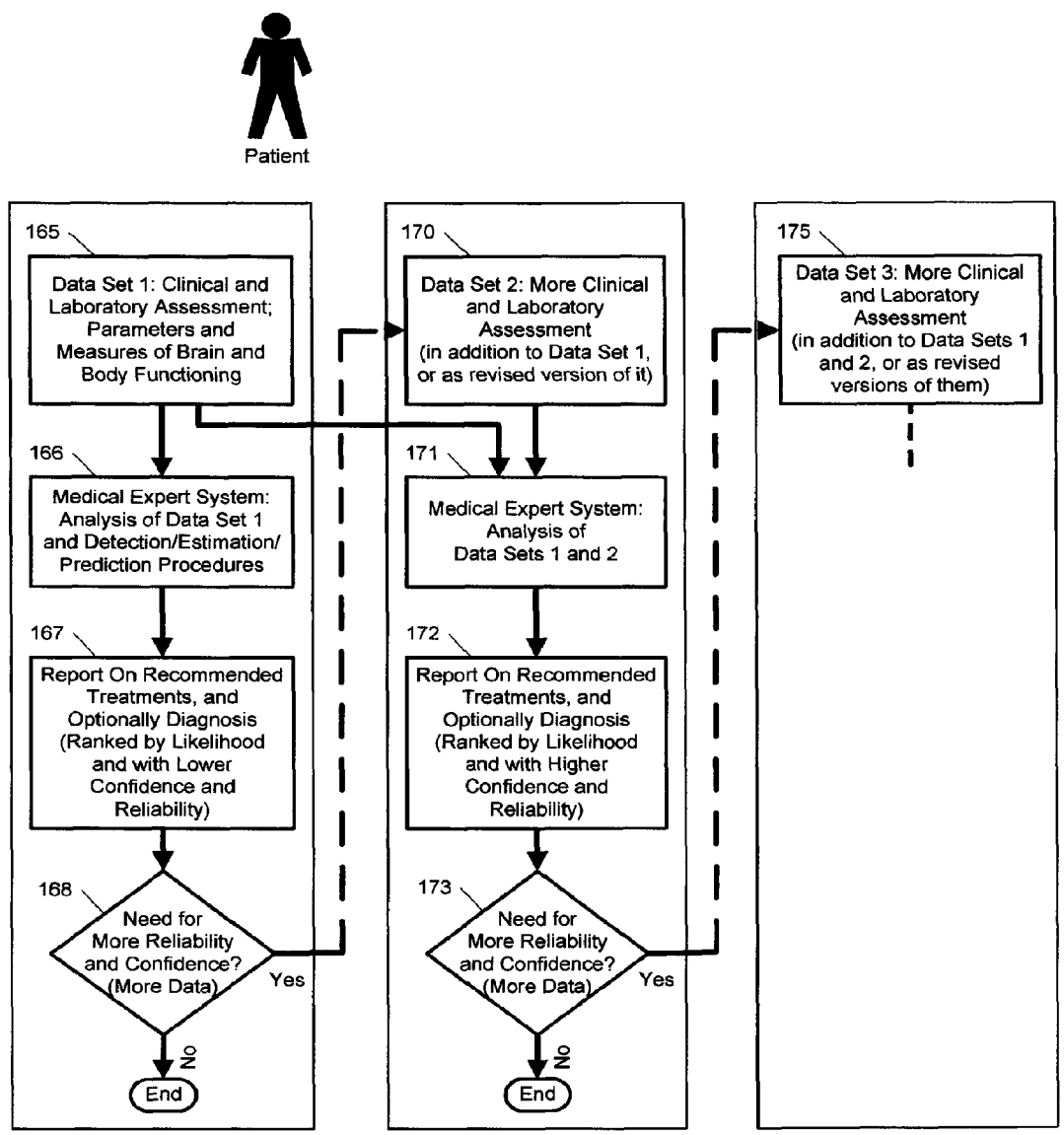
FIG. 7 is a flow chart illustrating an embodiment with interactive and multi-stage application of the medical digital expert system, with multiple sessions of data collection/measurement, data analysis, detection, estimation, and prediction. Only 3 sessions are shown, but it can be more.

(ii) Another element is the central signal/information processing and central data management and analysis subsystem. This is the part of the medical expert system which processes the data, extracts the critical and useful information, provides a list of diagnostic possibilities and predicts the treatment options. See 105 and 110. In doing so, this subsystem uses the training data containing information about the therapies used and clinical response in patients previously treated for this condition (106), employing machine learning and inference methodologies to find a list of the best treatment options that can be sent to the clinician/user. Here, the data base analysis duplicates and supplements the clinical acumen of the clinician. This subsystem could, optionally, identify key pieces of missing data and the communication and interface subsystem would send a prompt to the clinician requesting this further information. The expert system would then run its algorithm without this additional data then again if and when the missing data is provided. The data collection and data analysis results can be repeatedly calculated over several sessions until acceptable reliability is achieved or the medical expert system is not able to provide better results. This process is illustrated in FIG. 7.

(iii) A further embodiment is the improvement and adaptive update and adaptive learning subsystem: When a patient has complied with and completed the treatment and a valid outcome has been determined, this data can be entered into the training database. By collecting and using the pre-treatment data and determining the outcome of the treatment, through follow-up interview of the clinician and/or patient, the expert system goes through an update and development stage in which the whole signal processing and prediction/estimation subsystem and methodologies will be refined and adaptively improved (107 and FIG. 5). As validated post treatment response data, and optionally, diagnostic data, for each new patient accumulates and is added to the training database, the mathematical models of the estimators and predictors will be further improved (106 and 161). Machine learning techniques and information processing methods are applied to the medical diagnosis and treatment databases, and all computational parts of the system including pre-processing, estimation, detection, and prediction models are revised and re-trained when the size of the these databases are increased. The improvement and adaptation process can be done automatically with the adaptive and automatic training and update method, but to further enhance performance, a team of expert professionals can administer the process (151), and add (if needed) revised methodology or new machine learning and signal/information processing methods to the system.

The methods and systems of the invention can be further understood by referring to the Figures and the various aspects outlined below.

In one embodiment, optionally, the treatment recommendation procedure, medical diagnosis, and the estimation/detection of critical parameters, level or severity of the illnesses, diseases or conditions is performed through an interactive, iterative, multi-stage procedure whereby the first of a possible series of diagnostic or treatment recommendation reports is accompanied by a request for further data from laboratory testing, clinical examination or symptomatic enquiry, and then the additional data requested will be used to further refine the detection/estimation/prediction result in a subsequent re-analysis and further information processing. An example is shown in FIG. 7 where the data collection and data analysis can be repeated many times. This bi-directional information transfer, interactive interface and communication method reduces ambiguity in the diagnosis and treatment planning decisions and reports.

Central Information Processing and Data Management

Machine learning and inference methods are strongly dependent on the quantity and quality of the training set. Predictive performance in a properly designed system will improve as the number of training points is increased. Entering and analyzing data centrally at a remote processing site provides a reliable and unified framework for checking validity of measured signals, and then enriching the data base to improve the machine learning performance with the addition of new training data.

The medical digital expert system includes two databases: (i) treatment database, and (ii) medical assessment and diagnosis database. These are used for learning or training the diagnosis and medical assessment models, learning treatment-efficacy prediction/estimation models, training the structure of the medical digital expert system, and for making computational inferences The size of these databases are increased by adding new medical assessment, diagnosis and treatment-efficacy information collected from the user and the physician/clinician. The computational models for estimation, decision/detection and prediction of the medical digital expert system are revised and improved by gradual learning and adaptive training as new data becomes available.

The disclosed medical expert system may be used in two optional manners:

In one aspect all the measured data is sent to a remote station for signal processing and analysis, and receive the prediction results and recommended treatment options through the communication medium. This is shown in FIG. 1.

Figure 2:
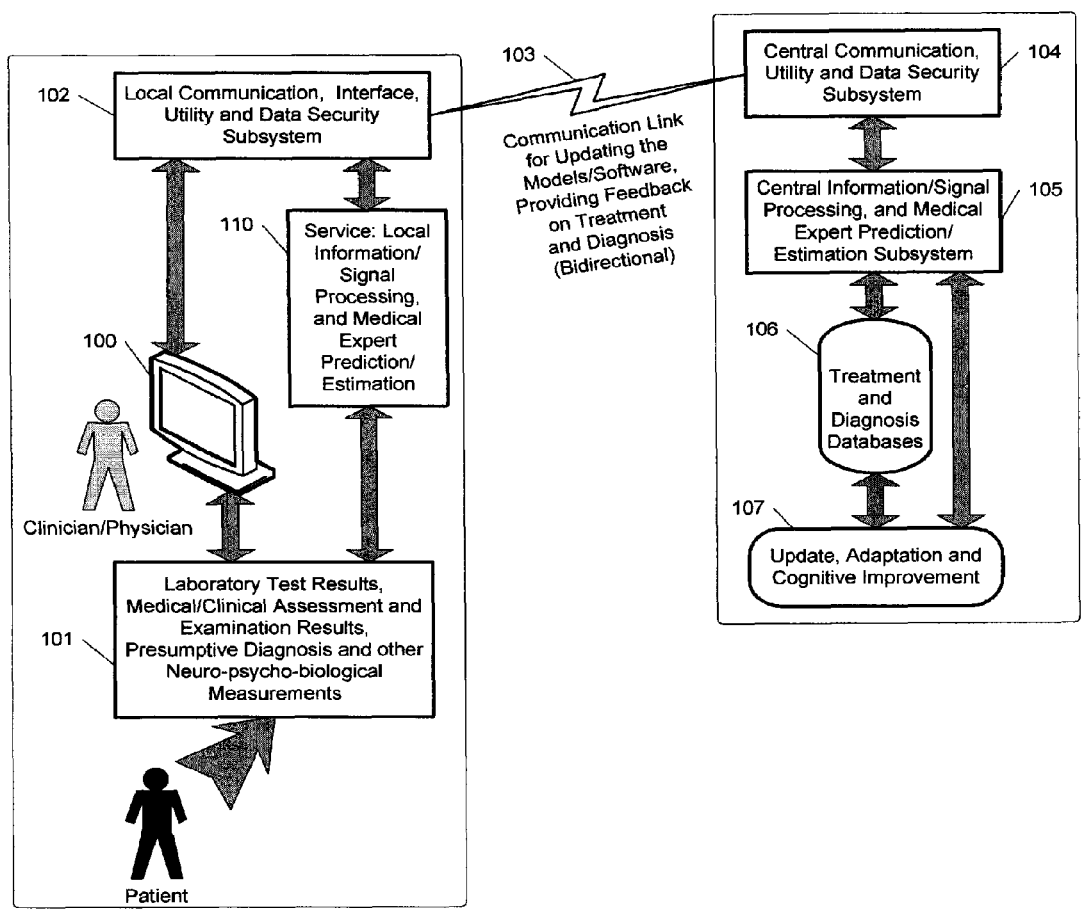
FIG. 2 illustrates schematically another embodiment of a system according to the present invention with local data/signal processing.
Figure 3:
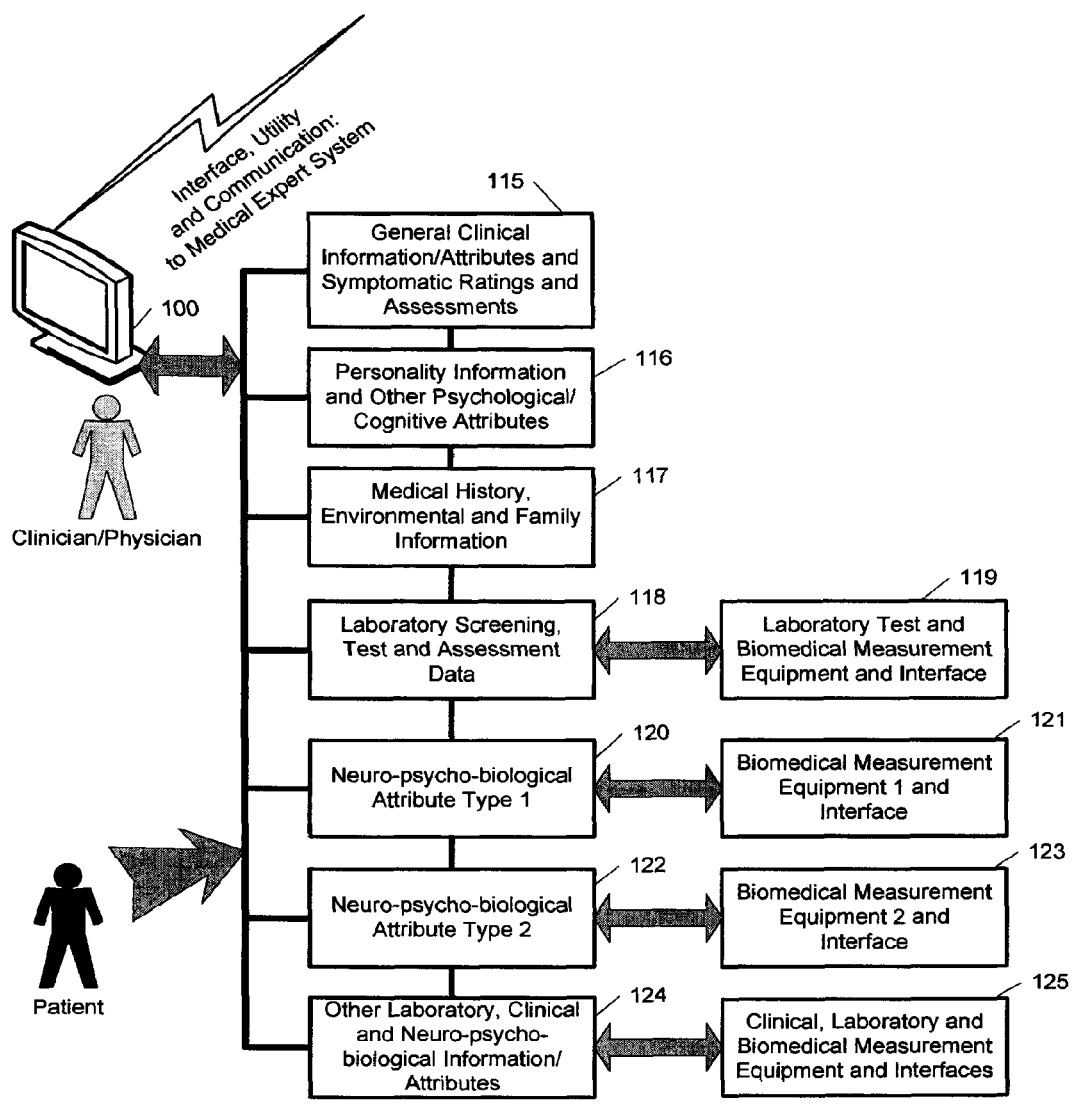
FIG. 3 is a flow chart illustrating one embodiment of data acquisition and neuro-psycho-biological assessment.
Figure 4:
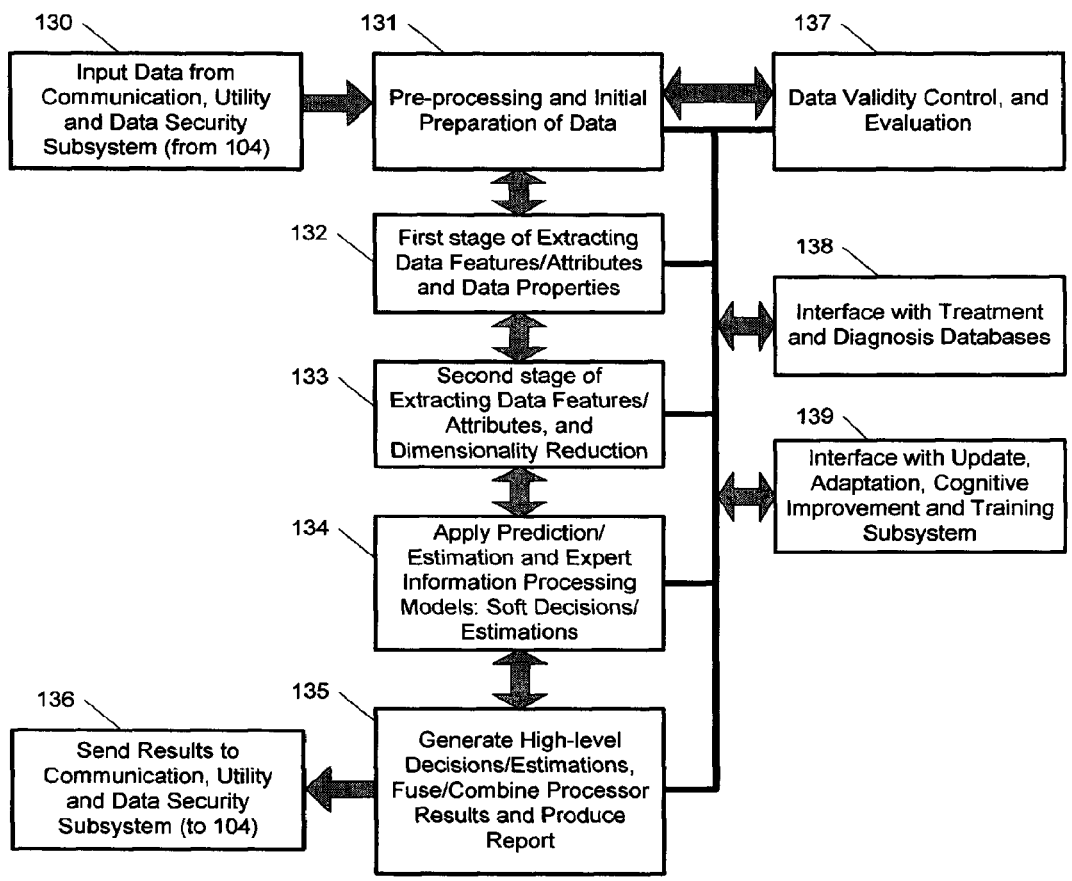
FIG. 4 is a flow chart illustrating one embodiment of an expert prediction, estimation and signal/information processing system according to the invention.

In another aspect the medical expert system's software and mathematical models are used locally (in the clinic or in the laboratory, etc.). The digital expert system can be down-loaded into the local computer from the remote central center, as it becomes available as illustrated in FIG. 2. In this case, the prediction/estimation can be done in the clinic without the need to communicate with the remote site. For more reliability and supervised data validity control, it is preferable to perform the improvement and adaptive update and learning process at the remote site, by communicating the treatment outcome and measured attributes to the central or remote center.

The key to improving the expert system and the signal processing methodology is the capability to gradually upgrade and learn when feedback on the predicted diagnosis and the outcome of the treatment is provided (see FIG. 5 and boxes 107, 138, 139, 160 and 161). The factors that can be updated by gathering new training data include: (i) the set of critical, important and discriminating attributes/features are updated adaptively, see 143 and 146, (ii) the signal processing methods and the predictor system are updated, see 147 and 148. The result will be a more reliable (and more experienced) digital system that is trained with a larger population of patients and with more variety of data and information.

In both of the above cases, the local physician employs a set of available standard clinical and laboratory assessments, (119, 121, 123, 125) and employs a user-friendly software or interface subsystem (100), to collect, encrypt and transfer the data to the remote processing site, or to calculate the treatment response probabilities locally (102, 103 and 104). See FIGS. 1 to 6.

For the medical diagnosis function of the medical digital expert system, the medical assessment or diagnosis training database is initially created formally in a clinical research trial or informally and outside a clinical trial by referring the patient to an expert physician/diagnostician to get a reliable reference diagnosis. The original diagnostic training set will be continually enlarged over time by contacting the patient and the patient's attending physician after the passage of a sufficient period of time for an illness or condition to more classically reveal itself syndromatically, through response to diagnosis-specific treatment, or after further testing. This new data increases the size of the diagnosis training database thereby resulting in improved performance and reliability of the medical diagnosis and medical assessment algorithms.

The Machine Learning Process

The machine learning procedure comprises at least two components. These include feature extraction and classification/prediction/estimation.

Features are a set of measurements taken from the object under test that allow us to discriminate which class the object belongs to. Features can be raw/direct measurements or can be processed information derived from measurements. Features are alternatively described as raw or processed versions of clinical and medical indicators, symptoms, numerical attributes such as laboratory test results and other measures of brain and body functioning, personality attributes, cognitive functioning, genetic markers and parameters quantized and encoded in numerical or categorical form such that they are understandable by computers and processing equipment for further analysis. In one example, in the case of mental and psychiatric illnesses and disorders, features are extracted from the patient's EEG measurements and other variables, after pre-processing. Features also include neurological, psychological, biological and clinical measurements as indicated earlier, as well as other personality indicators. The EEG feature set may include (but is not limited to) statistical attributes, random process parameters, coherency measures, correlation, higher-order statistics, wavelet analysis coefficients, autoregressive modeling coefficients, absolute and relative spectrum power levels in various frequency bands, the ratio of left-to-right hemisphere power in various frequencies, and the anterior/posterior power gradient in various frequencies, mutual information between sensors, spatial and temporal data model attributes, time-series model attributes, linear and non-linear dynamic process modeling features, features representing and extracting geometrical information of high-dimensional data, attributes representing the data in transformed and mapped space, and clustering and low-dimensional representation attributes, and combinations and transformations thereof. Those skilled in the art may be able to identify further features, without limiting the scope of this patent.

After initial feature extraction, there is a feature reduction and feature selection phase in which only the most relevant features attributes are found and stored for further processing (146).

Feature reduction and feature selection are parts of the medical expert system of the present invention. The expert system uses feature reduction and feature selection to provide a smooth estimator/predictor with a good generalization capability. This procedure is based on the realization that not all features from the feature set contribute equally to the clustering of the data. The task of dimensionality reduction or feature selection provides for compact representations of high dimensional data. In a preferred embodiment of the method of the invention only those features which exhibit the strongest mutual information and/or correlation and/or relevance between the feature itself and the training set target values are retained.

In one embodiment of the present invention, the feature selection is based on a mutual information criterion. The features selected are those which exhibit the highest mutual information with the training set. This method may be realized using the Kullback-Leibler divergence between approximations to the probability distributions of the feature set and the training set.

The difficulty with an information theoretic approach is that the selected features can exhibit high mutual redundancy. This is an undesirable situation that can lead to degraded performance. This situation can be corrected using the principle of minimum redundancy, wherein the features are selected using a criterion which is a compromise between high mutual information on the one hand and low mutual redundancy on the other.

In another embodiment, the selected subset of features is the subset which is most useful for the estimator/predictor method. This criterion combines feature selection with the estimation/prediction method and the goal is to generate the best final result with the greatest possible efficiency. This includes using wrapper and variable subset selection methods, nested subset selection, filters, direct objective optimization, or other methods or combinations of methods that achieve this goal.

In another embodiment, latent variable analysis, dimensionality reduction methods, principle component analysis, partial least squares, and kernelized versions of the above are used to extract a very-low dimensional representation of data that describe the most geometrically relevant information in the data. The result is then used in the estimation/prediction subsystem.

In another embodiment, geometric features are extracted using the "manifold learning" and geometric representation techniques, and geometric shape analysis techniques. Specifically, the assumption is made that the feature space lies on a low-dimensional nonlinear manifold, embedded in a higher-dimensional feature space (observation). Features can then be reduced by projecting the feature space onto this nonlinear manifold.

The Classifier/Predictor/Estimator System

The classifier/predictor/estimator is defined by "training or learning process". A large range of data from patients for which the prediction/decision/estimation outcome is known are collected. These data are referred to as "training data". The features for each patient are extracted from this training data. For each patient, these features define a point in an n-dimensional Euclidean space (assuming there are n features). In machine learning and inference methods these points will cluster into isolated groups in the n-dimensional space that correspond to the prediction outcome; i.e., responder or non-responder or, optionally, the diagnostic domain i.e. MDD, schizophrenia, bipolar disorder, etc. In the typical case, there is overlap between these groups; i.e., they do not separate cleanly. In a more complex scenario, each class may include several small clusters with some overlaps, and if they are separable and recognizable using some nonlinear discriminating functions, it is possible to construct a classification/prediction/estimation model based on the problem design. The job of the classifier/predictor is to mathematically segregate these clusters in an optimal fashion so that the probability of mis-classification or false-prediction is minimized. In another embodiment, the classifier/predictor/estimator explores statistical, dynamic, geometrical or structural and hierarchical information, or combinations thereof, inherent in the training data, and employs predetermined optimal criteria to construct the discrimination/decision/estimation schemes or models.

The classification/prediction/estimation and decision/inference techniques and models employed are derived from the computational signal/information processing and machine learning and inference methods and procedures which include, but are not limited to, parameter and model estimation methods, Bayesian learning and decision techniques, methods based on Bayesian estimation principles, kernel-based learning and classification methods, regularized prediction and regression methods, support vector regression and classification machines, dynamic decision-making methods, hidden Markov modeling methods, rule-based and fuzzy-learning techniques, fuzzy decision and estimation networks, structural, systematic, multi-level and hierarchical learning and inference methods, artificial neural networks, artificial intelligence, methods based on information theory, reinforcement learning, transductive learning and induction methods, and combinations and extensions thereof.

One of the computational data analysis and machine learning and inference methods and procedures used in the medical expert system is semi-supervised learning and inference methods. In semisupervised machine learning, in addition to labeled training data where the corresponding target variables are known, the information inherent in unlabeled clinical and laboratory information is used to construct a more efficient decision, estimation and prediction models and improve performance. In the case of medical diagnosis, for example, the unlabeled data corresponds to clinical and laboratory data derived from patients, but for which the true diagnosis or reference diagnosis is not known for the medical expert system, or not clinically confirmed. This means that the illness, disorder or condition corresponding to this data is not known. In the case of treatment selection or treatment-efficacy prediction, the unlabeled data corresponds to clinical and laboratory data of patients for which the final treatment outcome is not known, not recorded or not given to the medical expert system. This is an extension to the supervised learning in which all training data are completely labeled, and treatment-efficacy and diagnosis target variables are known. In semi-supervised machine learning and inference method, we have some labeled and some unlabeled training data. Because it is easier to collect unlabeled data, that shares the same characteristics and statistical, dynamic and geometric features as the labeled data, the performance of the detection, estimation and prediction methods and models are improved when semisupervised learning and inference methods are used. Various implementations of the technique include graph-based methods, generative models, probabilistic or statistical models, and combinations and extensions thereof.

Data Fusion

Data fusion is another component/subsystem of the medical expert system and method of the invention in which an optimal classifier/predictor/estimator architecture is provided by using lower-level or preliminary estimations and decisions (133, 135, 145, 148, 184). Several different advanced predictors/estimators in the system operate in parallel, each independently producing an estimation or decision on the treatment outcome given the measured data (184). In particular, for data points near decision boundaries, the predictors produce different outcomes. These results are then treated as soft decisions and combined using data fusion techniques such as statistical or heuristic data fusion (185). For example, the statistical learning framework offers rigorous methodology for this purpose, in that the probability dependencies between the outcomes and statistical properties of the soft decisions are learned by using the training set. This is illustrated schematically in FIGS. 4 and 5.

Figure 8:
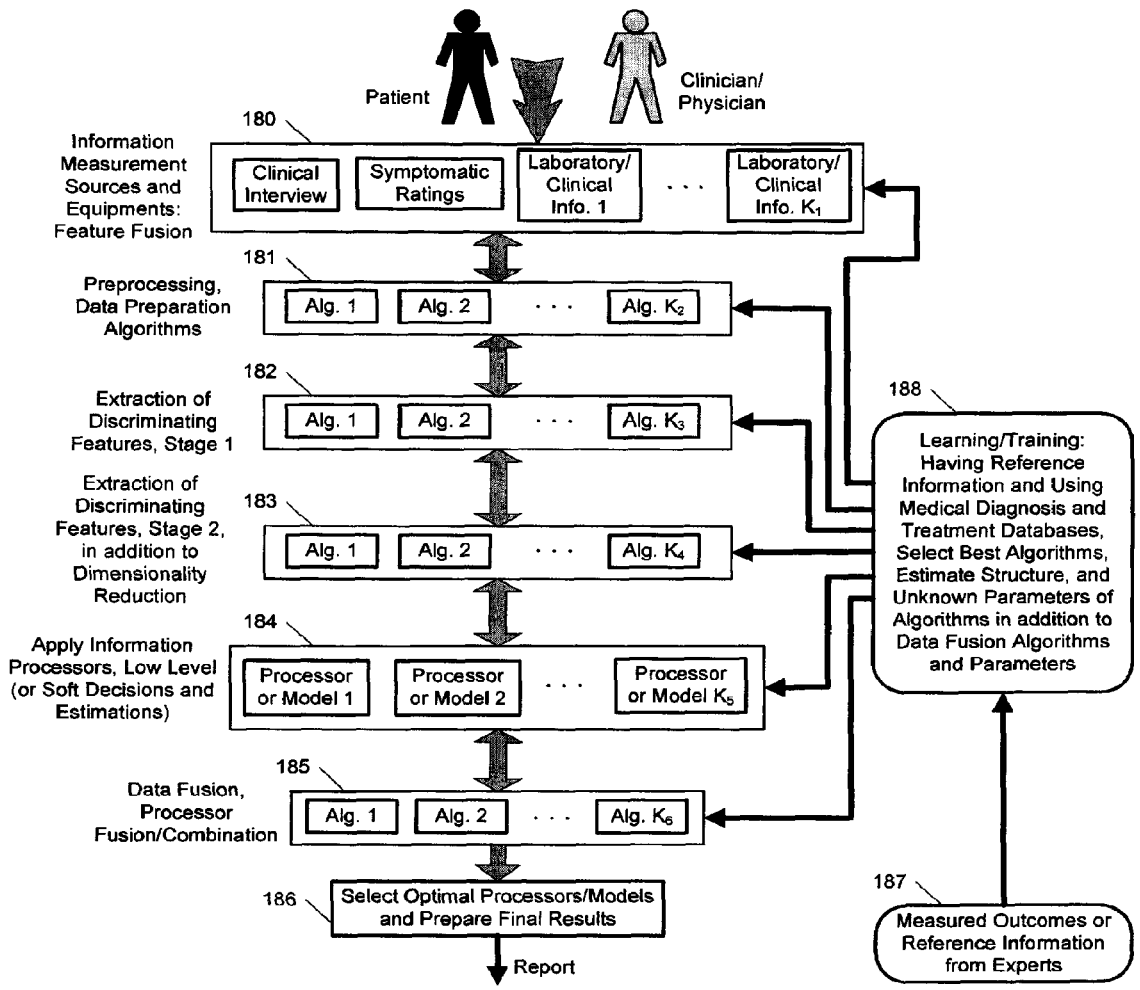
FIG. 8 is a flow-chart illustrating an embodiment using data fusion procedure (including feature level data fusion, and processor fusion).

There are currently accepted medical diagnostic classification systems and treatment guidelines that an expert clinician/physician uses when diagnosing and devising a treatment plan for a patient. Such known rules can be encoded and implemented digitally in a comprehensive medical data management, data interface, database and user-interface system (FIG. 7), and incorporated as part of the "digital clinician" or "medical digital expert system". There are also some unknown parameters and uncertainties involved in standard medical guidelines, published diagnostic classification systems and rules. For example, for each rule, the unknown parameters include a decision threshold in the rule, and the contribution factor of each particular rule to the overall diagnosis decision variable or to the treatment-selection decision variable may not be recognized. The medical expert system uses fuzzy-decision-making, fuzzy networks, rule-based learning, evidence theory-based methods and inference methodologies as well as statistical and Bayesian decision networks, probabilistic graphical models, belief networks or their extensions to incorporate this. The system can then process the clinical, personal and laboratory information in a manner similar to that employed by an expert physician. Furthermore, the internal rules of the decision and estimation network/structure in the medical expert system can be improved by learning using an enlarged training set and by exploring complex relationships between data and diagnostic rules. The machine learning and inference methods described previously in this document are combined in a structured setup with rule-based methods and include the facility of learning these rules and the internal structure of the decision and estimation networks and improving them to resolve uncertainties by using the training data samples (FIG. 8). It adaptively updates the internal rules and mathematical models of the estimators, detectors and predictors (188). In doing so, the "medical digital expert system" or "digital clinician" of the present invention has the ability to analyze all the data available to an experienced physician. Furthermore the massive computational capacity of the digital system permits exploration of highly complex relationships and characteristics. This can reveal potentially useful but hidden information in clinical and laboratory data. In this way information technology and machine learning and inference methodology can be combined to provide an intelligent medical data management system to aid the clinician or physician in treating diseases of various types.

Data fusion occurs in two levels. The first level is 'feature-level data fusion' (180, 181) in which the data and information from variety of sources of information and features, including a variety of clinical and laboratory assessments and tests are combined in an efficient way. The second level is 'processor data fusion' (184, 185), which is alternatively called 'algorithm fusion', 'decision fusion', or 'classifier fusion'. During 'processor fusion', the results of a small library of preliminary or low-level processing models (detection, decision, assessment, estimation and prediction models) are combined such that the overall system provides more efficient and more robust results than each individual preliminary processor, in determining medical diagnosis and treatment planning. The parameters and structure of data fusion and processor fusion is determined using training data.

The medical digital expert system disclosed in this invention includes a machine learning, machine inference and computational learning and information processing procedure including the following key components: user-interface, data management, data communication, data encoding, data security, diagnosis and treatment data bases, data pre-processing, feature extraction, feature selection, detection, estimation, prediction models and data fusion. For each component, there is a library of methods and techniques that can be employed. Based on the training databases, the expert system combines them in a data fusion and decision fusion procedure, such that the overall system performance is better or more robust than the individual methods. However, the result of each processing method can be accessed individually.

A short explanation of the present invention is presenting procedures, methods and systems for automation of medical diagnosis, treatment planning and treatment-efficacy prediction. It is based on advanced mathematical techniques for information pre-processing, feature extraction, dimensionality reduction, classification/prediction/regression models, and data fusion procedures. The models and the systems adaptively learn through training and efficient use of information in available reference databases that are constantly being augmented with new data.

The present invention illustrates digital means/models to automate the process of medical/clinical diagnosis and treatment planning. With reference to FIG. 8, the following information processing tasks and procedures are used:

(i). Feature Fusion: measurement of variety of medical and clinical information including clinical, laboratory, symptomatic ratings, etc. (180)

(ii). Pre-processing and data preparation (that are required to properly encode and prepare the information measured in the previous stage, and prepare them for future processes). (181)

(iii). Extracting relevant and discriminating features, stage 1: extracting various properties and attributes of data including geometric, statistical, temporal, dynamic as well as other computational modeling properties and attributes of the data. (182)

(iv). Extracting relevant and discriminating features, stage 2, in addition to dimensionality reduction and low-dimensional representation of the data. (183)

(v). Analyzing the data using information processors, low-level or soft decisions and estimations (184): The main data analysis is done here. Processors include classification, regression, estimations, decision (or detection), and prediction which are required to model diagnosis and treatment planning Many algorithms are used in parallel including models based on regularization theory, statistical methods, Bayesian methods, artificial neural networks, fuzzy networks, decision tree, and artificial intelligence methods.

(vi). Processor Fusion/Combination, in which the outputs of low-level information processors are combined and used to improve final performance. (185)

(vii). Training and adaptation: Using information from experts, recorded reference outcomes from patients and clinicians, diagnosis and treatment databases, the adaptive learning and training process and adaptation is done to select the best algorithms in each of the above stages and to estimate their structures and their unknown parameters. (187, 188)

Based on FIG. 7, similar to the procedure used by a human physician, the user-interface software of the "digital clinician" system works as follows: First a first set of clinical, laboratory data and symptomatic information (which includes the most basic and general information) are input to the software (165). Then the "digital clinician" or the "medical digital expert system" processes the data (166) and produces diagnosis/treatment-planning report, which is accompanied with confidence values, or decision likelihood values (167). The report can be some numbers or can be of graphical forms that show the level of confidence and reliability that the modeling and data analysis have on the result. Then the user may need more decision reliability and therefore, if wanted, goes to the next stage, in which the "digital clinician" asks for more specific clinical and laboratory information (170). Upon getting the new set of data, the "medical digital expert system" uses the collection of old and new sets of data to generate better results (171). And this procedure iterates for as long as the digital expert system and the user can handle.

The user-interface of the digital clinician system is based on a structure similar to a 'decision tree' where as one goes down the branches of the decision tree moving from general information to more specific information as the level of uncertainty is decreased. In the second level and beyond, the algorithm asks more specific questions that enables it to differentiate among possible solutions. It is a knowledge-based system that uses a structure similar to troubleshooting systems/software. The information that the software requests of the user is initially designed by the expert human physicians, incorporating and duplicating their best clinical practice (based on their experience and published clinical/medical treatment and diagnosis guidelines). The user-interface is connected via the communication medium to the central/remote data management and databases. It uses machine learning procedures to update and improve the initial structure and information that were given by human physician experts, and to make better estimates of the unknowns (such as the decision weight of each rule, and the detection threshold in each rule, etc.). The type and form of the information requested of the user in the second and subsequent stages are learned by the algorithm based on the experience derived through the use of the training databases. By employing cognitive adaptation and training procedures the performance of the algorithm or "digital clinician" improves with use.

A further aspect of the invention is the ability to deal with patients with "co-morbidities"; e.g., panic disorder, agoraphobia or dysthymia, etc. Patients with Co-morbidities are typically difficult to treat and may not be well represented in the training set, due to small sample size. If a statistical detection and estimation outlook is used in the present system and method, it is possible to model the effect of the co-morbidities as prior information which will affect the final posterior probabilities of the classes. The prior information can be attained from limited training data, if any, augmented with the experience of the physician.

In other aspects of the present invention, the methodology and medical digital expert system can be used to estimate the depth of anesthesia, or estimate the level of consciousness in the operating room or the intensive care unit. It also can be used in analysis of sleep disturbances, and sleep disorders. The invented system and methodology can be further used in applications where the goal is to assess, control and monitor health, physical or medical conditions of an individual undergoing any treatment or undergoing any medical or physical assessment and experiment.

In another embodiment and application of the present invention, the invented methodology and "medical digital expert system" is used in analysis, medical diagnosis and detection of various forms of stimuli, agents, or conditions, or in estimating medical critical parameters, indices, indicators, level or severity characterizing any disease, disorder or condition. For example, the expert cognitive system can be used to study the effect of a particular medicine on patients, or in pharmaceutical research and development, or to detect and analyze the effect of various chemical, biochemical, radio-isotopes, etc. The system could detect, in an individual person, heightened vulnerability or risk of developing a disease in future.

In another embodiment, the "digital clinician" or the "medical digital expert system" is used to estimate indicators or critical parameters of a condition, or to detect the presence of a condition when the condition is changing over time. For such cases, the medical diagnosis and treatment planning can be done by collecting all available clinical and laboratory data at each consecutive time step, then analyzing and reporting the results in each time. A second more efficient option involves measurement and collection of only the changes in clinical and laboratory data for analysis. Often many medical attributes, symptoms and parameters do not change over two consecutive time steps, and therefore there is no need for duplicating existing information.

Collection of clinical and laboratory data and other measured attributes of body and brain functioning can be done in three modes: 1) in the normal and resting-awake state, 2) during stimulus-driven, mood-induced, event-related or activity-evoked states, 3) during sleep, or some other altered level of unconsciousness e.g. general anesthesia or, 4) following administration of a medication. For example, in the case of conducting a mood-induction, evoked response or event-related recording, the activation or stimulus may include a set of predefined and controlled set of pictures, movies, sound-waves, music, magnetic, electric, electromagnetic, ultrasonic, or optical stimulation, biochemical, emotional, chemical stimulus, medical isotopes, and emotional stimulus, etc, or combinations thereof. As another example, the stimulus or activation procedure can be personal and individual-based, such that it is designed for the particular patient under study, and can be derived, for example, from the patient's own personal experience and life story. In this type of testing, the relevant information may be enhanced and while at the same time the influence of unwanted and random interference/noise may be reduced.

The method can be useful at both the specialist and general practitioner level. In certain conditions, the system can also be used by patients or researchers. The invented system would allow clinicians who do not have ready access to experienced specialist consultants to initiate therapy with some reasonable expectation of good outcome. Acknowledging the likely heterogeneity within currently established diagnostic categories, even the experienced specialist consultant might use this system to assist with the formulation of treatment recommendations. This may be particularly true with regard to the identification of clinical and biological features whose predictive relationships are highly subtle and apparent only when considered together in a multidimensional space that cannot be easily visualized by the human mind.

Increasing the effectiveness of determining first treatment choice will have broad economic and humanitarian implications for the patient, the clinician and the health care insurer.

Finally, the invention also encompasses program products, hardware, data management, medical diagnosis and treatment databases and medical data banks, control, processing, security, communication and user-interface software, equipment and systems comprising a system or digital or computerized or intelligent or automatic medium having encoded instructions and methods for causing a computer, or digital system/equipment to perform any or all of the methods of present invention.

Examples of Technical Detailed Implementation Procedure and Models

A few examples of technical detailed implementation procedures and embodiments of the information processing procedure in medical expert system will be described in the following. First, some preliminary methods and processors used in the medical expert system are illustrated, and then the data fusion and high-level decision/estimation methods are described.

In the treatment selection problem, given a set of training patterns from each class (responders' and 'non-responders' to treatment), the objective is to construct classification, regression and treatment-efficacy prediction models by solving an optimization problem based on the optimality criterion and the information in the training data set.

One method of building these numerical models is based on criterion of minimum regularized error, which is a trade-off between minimizing the model complexity and minimizing modeling error. One specific example is using regularization method translated to establishing decision boundaries in the feature space which effectively separate patterns belonging to different classes. In one type of such a preliminary processor, the direct discriminant function-based technique is used, where well-behaved and differentiable parametric forms of the decision boundaries and decision/estimation functions are specified, based on the regularization theory, or based on other determined optimality criterion. Then optimum estimation/decision function or decision boundaries are found using the training patterns.

The other types of preliminary processors are the ones based on the statistical/probabilistic and Bayesian estimation and detection criteria. In this type, the decision models or estimation functions are determined by the probability distributions, statistical relationships, and statistical optimality criteria. The Bayes decision criterion based on average decision cost minimization is the most effective in the probabilistic sense. The probability distributions are numerically estimated using the training data. In the 'parametric approach', a particular form for the conditional probability density (e.g., multivariate Gaussian model) is assumed which has some unknown parameters that are then estimated through learning. In the 'non-parametric approach', or 'distribution-free' statistical methods, like the Parzen window method, the conditional densities are estimated directly. Other types of statistical classification or regression models use the criterion of minimum probability of error, the criterion of maximum likelihood, or the criterion of maximum posterior probability to find model parameters.

The other types of preliminary processors are the ones based on other criteria of efficiency and performance, in which a numerical optimization problem is solved that corresponds to finding unknown classification, regression or prediction models based on a specific optimality criterion, and subject to a set of constraints. The constraints define the numerical properties and complexity of the model, and also define the relationship between training data (measured input data versus outputs or target values). In the data fusion setup, we use a number of models and processors, and some of the optimality criteria that are used to build these models include: minimum number of errors, minimum regression error, minimum classification error, minimum model complexity, minimum of combination of model complexity and modeling error which is also called as minimum regularized error, minimum probability of error, minimum prediction error, minimum false alarm, minimum estimation error, minimum decision cost, minimum stochastic complexity, maximum pattern-separation margins, maximum likelihood, or combinations thereof.

The neuro-psychological, symptoms, clinical and laboratory information obtained from the patient makes a multi-dimensional observation or measurement vector representing characteristics of the patient in the space of all possible values defining all patients. Assume that $N_C$ possibly relevant features of i-th data epoch corresponding to a patient are put together in a vector $x_i$, and the associated treatment outcome/efficacy or, optionally, associated medical diagnosis is denoted by target variable $y_i$, where $i=1, \ldots, M_t$ in which $M_t$ is the number of patients in the training database. Note that the feature vector $x_i$ can be viewed as a point in $N_C$ dimensional space.

Given training data set $D_t$ at time step t, $$D_t = \{(x_i, y_i), i=1, \ldots, M_t\}$$

$$x_i \in R^{N_C}, y_i \in R$$

The problem is to estimate a smooth mapping function $f: R^{N_C} \to R$ using the data set $D_t$. In more general case, the target or system output is a vector denoted by $y_i \in R^{N_o}$, where $N_o \leq 1$, however, for simplicity, the case of $N_o = 1$ is discussed. In the treatment selection problem, for example, function $f$ is the discriminative function and after discretizing it, the decision/selection tool is obtained. The data model is assumed to be $$y_i = f(x_i; \Theta) + n_i$$

$$i=1, \ldots, M_t$$

where $n_i$ are independent additive random variables, (modeling measurement noise, etc.), whose characteristics and probability distribution is unknown. $\Theta$ represents the set of unknown parameters and unknown structure of the model function $f$ which are to be estimated using the machine learning procedure and method employed.

An initial stage of information processing is reducing the dimensionality of features. In one embodiment, for selecting a small subset of appropriate features/attribute relevant to the regression or classification problem, the maximal statistical dependency criterion based on 'mutual information' is used. Assuming that both x and y data are discretized (or quantized), the mutual information between two discrete random variables x and y is defined as follows $$M(x; y) = \sum_{y_l \in Y} \sum_{x_l \in X} p(x_l, y_l) \log \frac{p(x_l, y_l)}{p_X(x_l) p_Y(y_l)}$$

where it is assumed that x can take a set of values indexed by $x_i$ (in a collection denoted by X), and y can take a set of values indexed by $y_i$ (in a collection denoted by Y). Here, X denotes the set of one particular feature out of all $N_C$ features derived from training samples. The number of examples in X is $M_t$. p(x, y) denotes the joint probability distribution function of x and y, and $p_X(x)$ and $p_Y(y)$ are the marginal probability distribution functions of x and y, respectively.

Therefore, when x and y are both discrete, (i.e., for discrete or categorical feature variables), the summation operation in the above equation can be used to calculate the mutual information. In this case, computing mutual information is straightforward, because both joint and marginal probability tables can be estimated by tallying the samples of categorical variables in the data.

When at least one of the variables x and y is continuous, their mutual information is computed using the following integral form $$M(x; y) = \int_X \int_Y p(x, y) \log \frac{p(x, y)}{p_X(x) p_Y(y)} dx dy$$

Intuitively, mutual information measures the information that x and y share: it measures how much knowing one of these variables reduces our uncertainty about the other. Mutual information quantifies the distance between the joint distribution of x and y and what the joint distribution would be if x and y were independent. It is a measure of dependence in the following sense: M (x; y)=0 iff x and y are not dependent, i.e. independent, random variables.

For continuous feature values, it is often difficult to compute the integral in the continuous space based on a limited number of samples. One solution is to incorporate data quantization and discretization as a preprocessing step. For example, we can discretize each element of a continuous feature using its estimated statistical average value μ and its standard deviation value σ. For example, one can have three variable regions representing three discrete levels of the feature as follows:

$$\{(-\infty, \mu-\sigma], [\mu-\sigma, \mu+\sigma], [\mu+\sigma, \infty)\}$$

For discretizing into 5 steps, one option is using the following margins: $\mu-3\sigma/2$, $\mu-\sigma/2$, $\mu+\sigma/2$ and $\mu+3\sigma/2$.

An alternative solution is to use a density estimation method (e.g., Parzen windows) to approximate the mutual information. Given $M_t$ samples of a generic multidimensional feature vector x, the approximate density function denoted by $\hat{p}(x)$ has the following form $$\hat{p}(x) = \frac{1}{M_t} \sum_{1}^{M_t} g_h(x - x_i)$$

where $g_h(\cdot)$ is the Parzen window function as explained below, $x_i$ is the i-th sample, and subscript h denotes the width of the window. With the properly chosen $g_h(\cdot)$ and h, the estimation $\hat{p}(x)$ will converge to the true density $p(x)$ when $M_t$ is very large. The function $g_h(\bullet)$ can be chosen as a Gaussian window as follows $$g_h(z) = \frac{1}{(2\pi)^{n/2} h^n \sqrt{\det(C_z)}} \exp\left(-\frac{z^T C_z^{-1} z}{2h^2}\right)$$

where $z=x-x_i$, n is the dimension of the sample vector x, and $C_z$ is the covariance of z. $\det(C_z)$ denotes the determinant value of the covariance matrix $C_z$.

When n=1, $\hat{p}(x)$ returns the estimated marginal density; when n=2, one can use the above Gaussian window definition to estimate the probability density of bivariate variable (x,y), i.e., p(x,y), which is actually the joint density of x and y. For the sake of numerically robust and easy estimation, for n≥2, the matrix $C_z$ can be assumed to be diagonal.

In maximal relevance criterion, the selected features $x_i$ are required, individually, to have the largest mutual information with the target class variable y, reflecting the largest dependency on the target class. Therefore using this ranking criterion one can select $N_i$ features out of $N_C$ candidates, which are then used in building discrimination and prediction functions.

However, it is likely that features selected according to maximal-relevance criterion could have rich redundancy, i.e., the dependency among these selected features could be large. When two features highly depend on each other, the respective discriminative power would not change much if one of them were removed. Therefore, a more optimal choice is to select features that are both relevant (dependant to target class variable) and also has minimum redundancy.

One suboptimal implementation of the above idea using 'incremental search' method is explained next. Suppose that the set of $N_i$ best features to select is denoted by A, and the set of all $N_C$ available candidate and possibly relevant features is denoted by X. The first member of A is the feature with maximum mutual information with the target value y. Then, suppose we already have $A_{m-1}$, the feature set with m−1 best features. The task is to select the m-th feature from the remaining set $\bar{A}=\{X-A_{m-1}\}$. This can be done by solving the following optimization problem which implements a tradeoff between having both maximum relevance and minimum redundancy $$\max_{x_j \in \bar{A}} \left\{ M(x_j; y) - \eta \frac{1}{m-1} \sum_{x_i \in A_{m-1}} M(x_j; x_i) \right\}$$

where η>0 is the regularization or trade-off parameter. The best value for the regularization parameter can be found using a simple grid search, and cross-validation, for example.

Another way of dimensionality reduction, clustering, and low-dimensional representation is using manifold learning as well as kernel 'principal component analysis' (PCA) method, to be described next. The basic or linear PCA method finds the subspace that best preserves the variance of the data that have linear structure. By the use of suitable nonlinear features, one can extract more information.

Kernel PCA first maps the data into some feature space F via a (usually nonlinear) function Φ, and then performs linear PCA on the mapped data. In medical expert system, it is one example of the methods used for dimensionality reduction, as well as low-dimensional representation. Low-dimensional representation is another optional output of the 'expert system', and given the test data, it can report the projection of test data onto the 2D or 3D space, and show the geometric relationship and similarity to training samples.

Kernel PCA is based on a kernelization approach. Many techniques (such as the basic support vector machine, that will be described next), result in linear decision boundaries and require only inner-product operations on the input data. It is possible to produce nonlinear decision boundaries in the feature space by transforming a feature vector $x_i \in R^{N_C}$ into another space F by defining a new vector Φ(x) for some nonlinear function Φ(•). However, a more efficient method of introducing nonlinearity is to compute inner products of the form $\Phi(x_i)^T \Phi(x_j)$ using kernel representations, where $x_i$ and $x_1$ are any two input feature vectors in $R^{N_C}$, as follows $$\Phi(x_i)^T \Phi(x_j) = K(x_i, x_j)$$

This procedure allows us to compute the value of the inner product in F without explicitly carrying out the transformation Φ(•).

One example of kernel function is a Gaussian kernel (with parameter σ), defined as follows $$K(x_i, x_j) = \exp\left(-\frac{1}{2\sigma^2} \|x_i - x_j\|^2\right)$$

The other kernel that can be used is d-th order polynomial kernel, defined as $$K(x_i, x_j) = (\mu x_i^T x_j + 1)^d$$

where μ is a parameter defining the polynomial, and d>0 is the polynomial degree. The simplest kernel function is the linear kernel defined as $K(x_i, x_j) = x_i^T x_j$. The other option is sigmoid kernel function which is defined as follows $$K(x_i, x_j) = \tanh(\zeta(x_i^T x_j + \theta))$$

where ζ and θ are fixed constants, which are design parameters. A kernel should satisfy the Mercer conditions.

A conic combination of kernel matrices has the properties of a single kernel matrix and therefore can be used as a kernel. A conic combination of set of kernel matrices indexed by h means $\Sigma_h \tau_h K_h$, where $\tau_h \geq 0$. First we make the assumption that we are dealing with centered data, i.e., $$\frac{1}{M_t} \sum_{i=1}^{M_t} \Phi(x_i) = 0.$$

Then the covariance matrix in F is $$C = \frac{1}{M_t} \sum_{i=1}^{M_t} \Phi(x_i) \Phi(x_i)^T$$

Covariance matrix C can be diagonalized by the eigenvalue decomposition $$Cv = \lambda v$$

where we have the fact that each eigenvector v with the corresponding eigenvalue $\lambda \neq 0$ can be expressed as $$v = \sum_{i=1}^{M_t} \alpha_i \Phi(x_i)$$

which means that each eigenvector lies in the span of Φ-images of the data set. Using the above facts and relationships, defining the $M_t \times M_t$ Mercer kernel matrix K with elements $K_{ij} = K(x_i, x_j) = \Phi(x_i)^T \Phi(x_j)$, and by some manipulations, we obtain in the following eigenvalue decomposition problem $$K\alpha = M_t \lambda \alpha$$

where $\alpha = [\alpha_1, \ldots, \alpha_{M_t}]^T$. Using Mercer kernel by the above definition, we avoid dealing with the mapped data explicitly. Normalizing the solution $v_j$ in F (i.e., $v_j^T v_j = 1$), translates into $\lambda_j(\alpha_j^T \alpha_j) = 1$.

To extract nonlinear principal components, we compute the projection of the Φ-image of a data point $x_i$ onto the j-th eigenvector in the feature space by $$z_{ij} = v_j^T \Phi(x_i)$$
$$= \frac{1}{\sqrt{\lambda_j}} \sum_{h=1}^{M_t} \alpha_{jh} K(x_h, x_i)$$
$$= \sqrt{\lambda_j} \alpha_{ji}$$

where $\alpha_{jh}$ denotes the h-th element of vector $\alpha_j$.

The low-dimensional representation of a data vector $x_i$ is computed as follows: First, calculate the kernel matrix using all data set. Second, compute m largest eigenvalues (in decreasing order) of kernel matrix K, and normalize them using relation $\lambda_j(\alpha_j^T \alpha_j) = 1$. Third, compute the projection of Φ($x_i$) onto corresponding eigenvectors. Finally the corresponding m-dimensional representation of $x_i$ is as follows $$z_i = [z_{i1}, \ldots, z_{im}]^T$$

The projection of $x_i$ onto the first m principal components in F can be written as follows $$\text{Proj}\{\Phi(x_i)\} = \sum_{j=1}^{m} z_{ij} v_j$$

Note that if m is large enough to take into account all directions belonging to eigenvectors with non-zero eigenvalue, we will have $\text{Proj}\{\Phi(x_i)\} = \Phi(x_i)$.

In general, we can not use the assumption that average of Φ(x) is zero. By relaxing this assumption, we need to use $$\tilde{\Phi}(x_i) = \Phi(x_i) - \frac{1}{M_t} \sum_{h=1}^{M_t} \Phi(x_h)$$

instead of Φ($x_i$). After calculating the kernel matrix K from the training data set, the modified version $\tilde{K}(x_i, x_j) = \tilde{\Phi}R(x_i)^T \tilde{\Phi}R(x_j)$ needs to be used in the above procedure in place of previous version. The elements of the modified kernel matrix can be written as $$\tilde{K}_{ij} = K_{ij} - \frac{1}{M_t} E_i - \frac{1}{M_t} E_j + \frac{1}{M_t^2} \sum_{h=1}^{M_t} E_h$$

where $$E_i = \sum_{j=1}^{M_t} K_{ij}$$

which means sum of elements in row i of matrix K.

In one embodiment, once the relevant discriminating features are found, many methods are used in parallel to build estimation, decision and prediction models. Then based on the training set, in a data fusion structure, the results of these models are combined to make the final outcome. In many of these models and processors, there is a tradeoff between model complexity on the one hand (which can lead to over-fitting) and model accuracy, which is essential for high performance estimation and estimation. One example of these methods solves a numerical regularization problem where the goal is minimize the following regularized risk functional $$R(f) = \frac{1}{M_t} \sum_{i=1}^{M_t} L(y_i, f(x_i; \Theta)) + \beta g(f)$$

where the second term, g($f$) is a stabilizer to minimize the model complexity of the function $f$, and the positive constant β is called the regularization parameter, which represents the relative importance of model complexity with respect to the performance measure (or model accuracy). $L(y_i, f(x_i; \Theta))$ is the loss functional which measures the discrepancy between target value $y_i$ and the value of the function $f$ for corresponding feature vector $x_i$.

As one preliminary model/processor based on the regularization theory, to build the estimation, decision and prediction models in the medical expert system, Vapnik's support vector machines (SVM) for regression is used, which exploits the idea of mapping input data into a high dimensional (often infinite) reproducing kernel Hilbert space where a linear regression is performed. The SVM regression corresponds to the epsilon-insensitive loss function defined as follows $$L(y_i, f(x_i; \Theta)) = \begin{cases} 0, & \text{if } |y_i - f(x_i; \Theta)| \leq \varepsilon \\ |y_i - f(x_i; \Theta)| - \varepsilon, & \text{otherwise} \end{cases}$$

where $\varepsilon > 0$. Training samples with small noise that fall in the flat zero (insensitive) region is not involved in the representation of regression or discriminating function. The function in this embodiment has the following form $$f(x) = \sum_{j=1}^{M_t} (\alpha_j - \alpha_j^*) K(x_j, x) + b$$

$$\Theta = \{\alpha_j, \alpha_j^*, b\}$$

where K is the kernel function, $b \in R$ is a bias term, and $\alpha_j, \alpha_j^*$ is dual Lagrangian variables to be estimated. There are many options for kernel functions as described earlier. During the learning phase, the best kernel can be chosen such that it results in best performance.

The above function $f(x)$ is the solution to the following numerical convex optimization problem which has a global minimum solution $$\max_{\alpha,\alpha^*} -\frac{1}{2}\sum_{i=1}^{M_t}\sum_{j=1}^{M_t}(\alpha_i-\alpha_i^*)(\alpha_j-\alpha_j^*)K(x_i,x_j)-\varepsilon\sum_{i=1}^{M_t}(\alpha_i+\alpha_i^*)+\sum_{i=1}^{M_t}y_i(\alpha_i-\alpha_i^*)$$

subject to $$\sum_{i=1}^{M_t}(\alpha_i-\alpha_i^*)=0,$$
$$0\leq\alpha_i\leq\delta,$$
$$0\leq\alpha_i^*\leq\delta$$

where the constant $\delta$ controls the trade-off between the flatness/smoothness of function $f(x)$ and the amount up to which deviations larger than $\epsilon$ are tolerated. If $\delta$ is chosen too large, then it will fit the training data well, but may suffer from 'over-training', i.e., inability to generalize to new observations or unseen test data. On the other hand, if $\delta$ is chosen too small, it will likely generalize, but may suffer from a lack of accuracy. During optimization, the values of $\alpha_i$ become zero, except those corresponding to 'support vectors', which are finally needed for construct the function $f(x)$ to be used in testing phase.

In matrix notation, the SVM regression problem is written as the following convex minimization problem (more technically, a convex quadratic programming problem) where the goal is to find the vector z, $$\min_z\left\{\frac{1}{2}z^THz+z^Tv\right\}$$

subject to $$[1,\ldots,1,-1,\ldots,-1]z=0$$

$$0\leq z_i\leq\delta, i=1,\ldots,2M_t$$

where $$z=\begin{bmatrix}\alpha\\\alpha^*\end{bmatrix},$$
$$v=\begin{bmatrix}\varepsilon-y\\\varepsilon+y\end{bmatrix}$$
$$H=\begin{bmatrix}K & -K\\-K & K\end{bmatrix}$$

and $y=[y_1,y_2,\ldots,y_{M_t}]^T$, $\alpha=[\alpha_1,\alpha_2,\ldots\alpha_{M_t}]^T$, and $\alpha^*=[\alpha_1^*,\alpha_2^*,\ldots\alpha_{M_t}^*]^T$. Note that once the kernel function is chosen, and we have the training samples, the kernel matrix K will be known.

One method to solve the above optimization problem, is to use the Platt's 'sequential minimal optimization' (SMO) method which decomposes the main problem into subproblems of size 2, and then solves for the two $z_i$ analytically. So, in the SMO method, the whole problem is solved analytically without using numerical convex optimization routines.

See Smola, A. J. and B. Scholkopf (2004) "A tutorial on support vector regression," Statistics and Computing, 14: 199-222.

Appropriate values for design parameters including $\delta$ and $\epsilon$ can be determined using the cross-validation technique. For example, a simple procedure is using the leave-one-out cross-validation technique. First, a set of candidate appropriate values for the design parameter is selected. Then, one training data pair $(x_i, y_i)$ out of total $M_t$ data pairs is used as test, and the rest, which means the data set $D_t^{(-i)}$ defined as follows, is used for training $$D_t^{(-i)}=\{D_t-(x_i,y_i)\}$$

For each candidate design value, averaging the corresponding performance over all test samples $i=1,\ldots,M_t$, the best suboptimal design parameter will be found that yields the best average test performance. It is to be noted that this procedure can also be used in finding suboptimal design parameters of preliminary processors/models other than SVM, which are described in this document.

When constructing decision or classification functions using SVM, each single SVM processor only can do a binary classification. For multi-class classification, a decision architecture made up by 'one-versus-one', or 'one-versus-rest' binary classification units needs to be constructed.

Another preliminary processor is the regularized least squares regression (RLS) model. Based on the regularization problem defined previously, if the kernel matrix is defined by matrix K, in RLS method, the regression function is defined as follows $$f(x)=\sum_{j=1}^{M_t}a_jK(x_j,x)$$

$$g(f)=a^TKa$$

where $a=[a_1,\ldots,a_{M_t}]$ is the unknown vector to be estimated by solving the following system of equations $$(K+\beta I)a=y$$

in which I denotes the $M_t\times M_t$ identity matrix, and $\beta>0$ is the regularization parameter. Again any of the kernel functions, or a conic combination described previously, can be used in RLS.

Partial least squares regression is another preliminary processor. In partial least squares (PLS) regression method the goal is to predict a set of dependent variables using a set of independent variables or predictors. The prediction is done by extracting from the predictors a set of orthogonal factors called latent variables which have the best predictive power. PLS regression is particularly useful when we need to predict a set of dependent variables from a (very) large set of independent variables (i.e., predictors). PLS components are computed under the constraint of maximization of covariance between inputs and outputs and not only under the input variance maximization, [Rosipal2006].

Assuming in general that the dimensionality of target values is $N_o$, if we put all the input training data in $M_t$ by $N_i$ matrix X, and the target values are represented by $M_t$ by $N_o$ matrix Y, PLS regression decomposes both X and Y as a product of a common set of orthogonal factors and a set of specific loadings. It is assumed that $N_i>N_o$.

Compared to 'principal component analysis' (PCA), PLS regression finds components from X that are also relevant to Y. Specifically, PLS regression searches for a set of components (called 'latent vectors') that performs a simultaneous decomposition of X and Y with the constraint that these components explain as much as possible of the covariance between X and Y. This step generalizes PCA. It is followed by a regression step where the decomposition of X is used to predict Y.

The independent variables are decomposed as $$X = SP^T$$

such that $S^T S = I$
with I being the identity matrix. By analogy with PCA, S is called the 'score matrix', and P the 'loading matrix' (in PLS regression the loadings are not orthogonal). Likewise, Y is estimated as $$\hat{Y} = SBC^T$$
$$= XB_{PLS}$$

where B is a diagonal matrix with the regression weights as diagonal elements and C is the weight matrix of the dependent variables. The columns of S are the 'latent vectors'. When their number is equal to the rank of X, they perform an exact decomposition of X. Note, however, that they only estimate Y, (i.e., in general Y is not equal to Y). $B_{PLS} = (P^T)^+ B C^T$, where $(P^T)^+$ denotes the pseudo-inverse of $P^T$.

Any set of orthogonal vectors spanning the column space of X could be used to play the role of S. In order to specify S, additional conditions are required. For PLS regression this amounts to finding two sets of weights w and c in order to create (respectively) a linear combination of the columns of X and Y such that their covariance is maximum. Specifically, at the i-th iteration, the goal is to obtain i-th pair of vectors $s_i = X w_i$ and $u_i = Y c_i$ where $c_i$ is the i-th column of matrix C, with the constraints that $w_i^T w_i = 1$, $s_i^T s_i = 1$ and $b_i = s_i^T u_i$ is maximal. In each iteration, $w_i$ is calculated by $w_i = X^T u_{i-1}/(u_{i-1}^T u_{i-1})$. Then the vector $w_i$ is normalized to unity norm. After calculating $s_i$, the vector $c_i = Y^T s_i/(s_i^T s_i)$ is normalized to unity norm, before calculating $u_i$. After reaching convergence in calculating $s_i$ (by repeating the above calculation loop), the scalar $b_i = s_i^T u_i$ is calculated which constructs the i-th diagonal element of the matrix B.

After the extraction of the score vectors $s_i$ and $u_i$, the matrices X and Y at the i-th iteration are deflated by subtracting the rank-one approximations based on $s_i$ and $u_i$. In the above procedure, the procedure is re-iterated until X becomes a null matrix.

Kernel PLS regression is an extension of PLS and employs kernels to model nonlinear data relations. One type of this method is as follows: A linear PLS regression model in a nonlinear feature space is considered. First an output kernel Gram matrix is defined as follows $$K_o = YY^T$$

An input kernel Gram matrix $K \in R^{M_t \times M_t}$ is also defined, with elements at row i and column j defined as $K_{ij} = K(x_i, x_j)$ with a kernel function. Using these definitions, the estimates of $s_i$ and $u_i$ in nonlinear feature space can be obtained by reformulating the problem into a nonlinear kernel variant form as follows $$KK_o s_i = \lambda_i s_i$$

$$u_i = K_o s_i, i = 1, \ldots, M_t$$

Similar to the ordinary PLS method, a zero-mean nonlinear kernel PLS model is assumed. To centralize the mapped data in a feature space, the following centralization procedure must be applied $$K \leftarrow ZKZ$$

where Z is the centralization matrix $$Z = I_{M_t} - \frac{1}{M_t} 1_{M_t} 1_{M_t}^T$$

and $I_{M_t}$ is a $M_t$-dimensional identity matrix and $1_{M_t}$ denotes a $M_t \times 1$ vector with all elements equal to one.

At each step, after the extraction of the new score vectors $s_i$ and $u_i$, the matrices K and $K_o$ are deflated by subtracting their rank-one approximations based on the estimated $s_i$ and $u_i$. The process continues until the desired number m of latent variables is extracted. As in the linear PLS case, the effectiveness of the method results from the fact that the score variables $\{s_i\}_{i=1}^{m}$ are good predictors of Y. See Rosipal R. and N. Kramer, "Overview and recent advances in partial least squares," in Subspace, Latent Structure and Feature Selection Techniques, C. Saunders, M. Grobelnik, S. Gunn, and J. Shawe-Taylor, Eds. Lecture Notes in Computer Science, Springer, 2006, pp. 34-51.

Another preliminary processor used in the expert system is based on mixture of factor analysis. Factor analysis is a method for modeling correlations in multidimensional data, by expressing the correlations in a lower-dimensional, oriented subspace.

In basic factor analysis, assuming the measured/input data set is given by $X = [x_1, \ldots, x_{M_t}]$. The model assumes that each $N_C$-dimensional data vector $x_i$ was generated by first linearly transforming a $m < N_C$ dimensional vector of unobserved independent zero-mean unit-variance Gaussian sources (factors), $d_i = [d_{i1}, \ldots, d_{im}]$, translating by a fixed amount $\mu$ in the data space, followed by adding $N_C$-dimensional zero-mean Gaussian noise, $n_i$, with diagonal covariance matrix $\psi$. Expressed mathematically, the model is $$x_i = \Lambda d_i + \mu + n_i$$

where $d_i = N(0, I)$, $n_i = N(0, \omega)$, and where $\Lambda$, a $N_C \times m$ matrix, is the linear transformation known as the factor loading matrix, and $\mu$ is the mean vector of the analyzer. $N(\cdot, \cdot)$ denotes the multidimensional Gaussian distribution in which the first argument is its average or mean vector and the second argument is its covariance matrix. Integrating out $d_i$ and $n_i$, the marginal probability density of $x_i$ will be Gaussian about the displacement $\mu$, $$p(x_i | \Lambda, \mu, \psi) = N(\mu, \Lambda \Lambda^T + \psi)$$

However, the high-dimensional data lies, to a good approximation, on a low-dimensional manifold. For example, consider the data set consisting of many different images of the same digit, given in terms of the pixel intensities. This data has as many dimensions as there are pixels in each image. To explain this data we could first specify a mean digit image, which is a point in this high dimensional space representing a set of pixel intensities, and then specify a small number of transformations away from that digit that would cover small variations in style or perhaps intensity. In factor analysis, each factor dictates the amount of each linear transformation on the pixel intensities. However, with factor analysis we are restricted to linear transformations, and so any single analyzer can only explain well a small region of the manifold in which it is locally linear, even though the manifold is globally non-linear.

Mixture of factor analysis is one way to overcome this problem in which the data manifold is tiled. A mixture of factor analyzers models the density for a data point $x_i$ as a weighted average of factor analyzer densities $$p(x_i \mid \alpha, \Lambda, \mu, \Psi) = \sum_{s_i=1}^{S} p(s_i \mid \alpha) p(x_i \mid s_i, \Lambda, \mu, \Psi)$$

where, S is the number of mixture components in the model, $\alpha$ is the vector of mixing proportions, $s_i$ is a discrete indicator variable for the mixture component chosen to model data point i, $\Lambda=\{\Lambda^s\}_{s=1}^{S}$ is a set of factor loadings with $\Lambda^s$ being the factor loading matrix for analyzer s, and $\mu=\{\mu^s\}_{s=1}^{S}$ is the set of analyzer means. The last term in the above probability is just the single analyzer density, described previously.

By exploiting the factor analysis parameterization of covariance matrices, a mixture of factor analyzers can be used to fit a mixture of Gaussians to correlated high dimensional data without requiring an order of $N_C^2$ unknown parameters, or undesirable compromises such as axis-aligned covariance matrices. In an MFA each Gaussian cluster has intrinsic dimensionality m, or $m_s$ if the dimensions are allowed to vary across mixture components (indexed by s). Consequently, the mixture of factor analyzers simultaneously addresses both problems of clustering and local dimensionality reduction. The unknown parameters can be estimated using the expectation-maximization (EM) algorithm, or its extensions such as the variational EM, and variational Bayesian learning algorithms (Roweis, S. and Z. Ghahramani, "A unifying review of linear Gaussian models," Neural Computation, 11(2): 305-345, 1999).

Based on the example descriptions and embodiments above, the 'adaptive learning' refers to the case where new training samples becomes available and are added to the medical diagnosis and treatment planning data bases. This corresponds to having a larger training set $D_{t'}$ at a time t' greater than t, with size $M_{t'}$ where $M_{t'}>M_t$. Having a larger training set, the medical expert system performs a learning or training of all its information processing models/processors including estimation, decision and prediction models, feature extraction models, and also learning of its data fusion models and structures. The newly collected data is added to the medical diagnosis and treatment databases, and since it represents a larger sample of the population and/or represents a more diverse variety of medical conditions, therefore, the estimation, decision and prediction models built based on them will be more reliable and will have higher performance. For example, in the medical diagnosis problem, this can be illustrated by the fact that data points or features representing each illness or condition belong to some manifold in the high-dimensional space, make a particular combination of clusters, and have some specific statistical and dynamic properties, which all become easier to estimate by computational methods if more samples and more examples becomes available. More training data means more numerical stability in learning the models/processors. A similar explanation is true for treatment selection and treatment efficacy prediction problems. However, this is true if the new training data samples are reliable and accurate.

Also, in the example descriptions and embodiments above, there are two phases or two modes. The medical expert system works either in learning phase, or in operational/service/test phase:

(i) 'Learning phase' in which the structure and model of estimation, decision and prediction functions are estimated. For example, in the SVM method described previously, the learning stage corresponds to estimating the unknown parameters $\Theta$ based on the training data, and solving the numerical optimization problem. This means estimating the parameters $\{\alpha_j, \alpha_j^*; b\}$ and also determining appropriate (or approximately optimal) values for design parameters like $\{\epsilon, \delta, \sigma\}$, which defines the function $f(x)$. The adaptive learning procedure discussed in this invention corresponds to this phase.

(ii) 'Test, service or operational phase', in which based on already known models, the clinical and laboratory data, represented by feature vector x, is given to the expert system. Then the expert system estimates or predicts the target value y. To show the difference, we can call this estimate by $\hat{y}$, which might not be exactly equal to true value. However, the medical expert system tries to find the best estimate, which is as close as possible to the true value, based on a determined optimality criterion. Note that in the test phase, the medical expert system does not have access to the true target value y corresponding to test data x. The detection, estimation or prediction result is then reported back to the clinician/physician. This is the normal service mode of the medical expert system. Many numerical methods can be used to implement the data fusion, including statistical estimation and detection theory, Bayesian network, graphical decision/estimation models, evidence theory, possibility theory, fuzzy-logic, belief network, fuzzy network, neural networks, genetic algorithms, artificial intelligence, and pattern recognition algorithms.

The clinical and laboratory data that is measured for a patient may come from different types or sources of information (such as clinical ratings, EEG, MRI, radiology, laboratory assessment, pharmacogenetic data, medical history, etc.). Data of each source has different properties and require proper information preprocessing. We can refer to the data at the end of source-specific preparation and pre-processing stage of each information source as "raw feature data". The raw feature data goes through a feature extraction, further higher-level feature generation, feature ranking and discriminative feature selection.

Also, a collection of preliminary or low-level estimation/detection/prediction models (or processors) are employed which each use the discriminative features to calculate preliminary estimation, decision and prediction results. Each preliminary processor may use the feature data from one data source or from multiple sources. Each preliminary processing model has its own numerical properties, and special processors/models are superior in different cases, and the idea in data fusion is to combine these results in an optimal way for more accurate and more robust performance in treatment planning and optionally in medical diagnosis. Data fusion can be regarded as a data-reduction mapping from multiple inputs of information into a smaller number of outputs. The outputs or high-level results that the 'medical expert system' reports are numerical values for optimum treatment selection, treatment-efficacy prediction, and optionally, for medical diagnosis. Another less optimal option to perform the data fusion is to run the complete course of processing/analysis for each source of information separately, and then combine these high-level results afterwards.

There is cross-correlation, statistical dependency and shared information among estimates/decisions/outcomes reported by preliminary processors/models. In the following we will describe a simple implementation to use this kind of information among processors. During adaptive learning procedure, the best implementation of the data fusion model can be chosen using the training set and based on the determined optimality criterion.

For example, the cross-correlation among models/processors can be estimated. The other option is to de-correlate the preliminary outcomes. Also, there are cases we cannot estimate the cross-correlation, nor can de-correlate them. In the third case, the covariance intersection algorithm can be used, for example, in which a consistent final estimate is obtained. Ultimately the goal is to correct the error of each processor/model by the other processors/models. The basic assumption is that errors among processors/models are not the same for the same input data.

An example of processor fusion model is the 'linear opinion pool', in which the fusion output is a weighted sum of the probabilities from each model/processor.

$$P_{lin}(E|x) = \sum_{i=1}^{q} w_i P_i(E|x)$$

such that:

$$\sum_{i=1}^{q} w_i = 1,$$

and $$0 \leq w_i \leq 1,$$

$$i = 1, \ldots, q$$

where q is the number of all preliminary processors/models employed in the medical digital expert system. $P_{lin}(E|x)$ is the combined probability for an event E when employing preliminary results from all q models. $P_i(E|x)$ is the probability of the i-th model for event E given the input data x, and $w_i$ is the fusion weight. The 'minimum mean squared error'(MMSE) criterion, or 'minimum classification error' (MCE) criterion can be used to estimate the fusion weights.

The other method is 'log opinion pool', in which the fusion result is $$P_{log}(E|x) = \prod_{i=1}^{q} [P_i(E|x)]^{w_i}$$

Compared to linear opinion pool, the output distribution of the log opinion pool is typically unimodal. However, if any model assigns a probability of zero, the combined probability will be zero. Hence, with log opinion pool, each individual model has the capability of a 'veto', whereas in the linear opinion pool, the zero probability is averaged out with other probabilities.

Based on the task, the problem setup, and the optimality criterion, the fusion weights can be estimated. For example, for a classification problem with N classes, $y_i \epsilon \{E_1, E_2, \ldots E_N\}$ is a class label for input vector $x_i$. Let assume that each processor has N output units/functions corresponding to N classes. We want to construct a processor fusion such that the weights are class dependent. The linear opinion pool in this problem can be written as $$f_{lin}^{(n)}(x; w^{(n)}) = w^{(n)T} f^{(n)}(x), n=1, \ldots, N$$

where $w^{(n)} = [w_1^{(n)}, \ldots, w_q^{(n)}]^T$ and $f^{(n)}(x) = [f_1^{(n)}(x), \ldots, f_q^{(n)}(x)]^T$. The decision rule by the combined classifier will be:

decide $x \epsilon E_n$ if $$f_{lin}^{(n)}(x) = \max_{h} f_{lin}^{(h)}(x)$$

Assume that $y_i = [y_{i1}, \ldots y_{iN}]^T$ is an N dimensional target vector, whose n-th component is one, and the rest of the components are zero if $x_i \epsilon E_n$. Also assume that the $f_h^{(n)}(x_i; D_t^{(-i)})$ for n=1, ..., N and h=1, ..., q, denotes the output of the classification function in h-th processor for n-th class output unit, when the sub-classifier is trained based on data set $D_t^{(-i)}$. As defined earlier, $D_t^{(-i)}$ is the whole training data set without the pair $(x_i, y_i)$. Let $$g_i^{(n)} = [f_1^{(n)}(x_i; D_t^{(-i)}), f_2^{(n)}(x_i; D_t^{(-i)}), \ldots, f_q^{(n)}(x_i; D_t^{(-i)})]^T$$

Then an estimate of the fusion weights can be found by solving the following minimization problem, See the paper by Ueda in Sinha, A., C. Huimin, D. G. Danu, T. Kirubarajan and M. Farooq, "Estimation and decision fusion: a survey", Proceedings IEEE Int. Conf. on Engineering of Intelligent Systems, pages 1-6, April 2006.

$$\hat{w}^{(n)} = \sum_{i=1}^{M_t} \left( w^{(n)T} g_i^{(n)} - y_{in} \right)^2,$$

n=1, ..., N
subject to $w_h^{(n)} \geq 0$, h=1, ..., q

Another simple 'processor fusion' method is to use a voting/ranking procedure, where each processor/model generates a decision variable instead of a continuous score. There are many voting techniques, including the majority vote. Ranking techniques are useful when the problem is to classify the input data into numerous classes. They use the class set reduction method to reduce the number of class candidates without losing the true class. By reducing the number of classes and reordering the remaining association possibilities, the true class will move to the top of the ranking. There are other methods such as fuzzy integral method, which combine the beliefs of various models into an overall consensus belief, not just their respective decisions. See Sinha, A., C. Huimin, D. G. Danu, T. Kirubarajan and M. Farooq, "Estimation and decision fusion: a survey", Proceedings IEEE Int. Conf. on Engineering of Intelligent Systems, pages 1-6, April 2006., and Torra, V., "Information fusion in data mining", Springer, 2003.

Another option for 'processor fusion' is divide-and-conquer approach which isolates the types of inputs from which a specific processor performs well, and directs these inputs accordingly. A sequential approach uses one processor first, and invokes others only when it fails to yield a decision with sufficient confidence.

Statistical and Bayesian data fusion is another approach that medical expert system can use, which is based on estimating statistical properties of processors and then combining them in a Bayesian decision/estimation setup.

'Fuzzy logic' is a form of multi-valued logic derived from 'fuzzy set theory' to do reasoning that is approximate rather than precise. A fuzzy neural network or neuro-fuzzy system is a learning machine that finds the parameters of a fuzzy system (i.e., fuzzy sets, fuzzy rules) by exploiting approximation techniques. A fuzzy decision system can incorporate linguistic rules instead of learning examples as prior knowledge. The input and output variables can be described linguistically. The fuzzy system must be tuned or trained to resolve the uncertainties, and find unknown parameters, since usually there are incomplete, wrong or contradictory knowledge about how to make the decision.

Such techniques enable the invention to be provided with means for establishing a feature data scheme or model relating feature data and treatment outcome or response (or other assessment status).

Training Data Acquisition Examples

The invention relies on the availability of reliable training data. Since gathering training data is expensive, the data acquisition task must be executed with considerable care. The training data acquisition step in our experimental group proceeded only after careful diagnosis of our study subjects using the Structured Clinical Interview for DSM diagnosis and application of inclusion/exclusion criteria. In the active community clinic where such cumbersome interviews cannot be employed, diagnostic certainty will likely be reduced, though this can be minimized through the use of diagnostic symptom checklists, which have been shown to increase the reliability of psychiatric diagnosis (See FIG. 3).

In the case of treating major depressive disorder, and when using anti-depressant medication therapy, for example, in a normal routine, after an optional psychotropic drug washout period (to remove the potential contaminating effects of these drugs on the EEG signal) the data acquisition step would begin. Dosing of medications could follow published dose guidelines. Depression and anxiety severity could be measured at baseline and at two-week intervals during treatment with antidepressant medication.

In one embodiment of the present invention, when the illness or condition is related to brain, or classified as a neurological, or psychiatric illness or disorder, the EEG measurements can be recorded using any approved general-purpose EEG system. The resting-awake EEG recording, through multiple sessions of eyes-closed and eyes-open status, could be completed as one option, or various sensory, loudness dependent auditory, induced emotion, stimulus driven, and other evoked response potentials, P300 potentials and combinations thereof could be optionally measured.

In one embodiment of the present invention, in the case of a mental or psychiatric illness, as an example, in addition to EEG recordings, numerous clinical variables can be collected using questionnaires, depression and anxiety rating scales, symptom-checklists and personality and cognitive assessment. For MDD, the range of data collected could include co morbid diagnoses, age, sex, marital status, education level, social support measured using the Perceived Social Support from Friends and Family rating scale (PSS) or similar scales, quality of life measured using the SF-36 or similar quality of life rating instruments. Previous medication therapy and past compliance could be measured using a modified version of the Michigan Adequacy of (previous) treatment scale (MATS) or similar instrument. Psychological and personality attributes such as neuroticism and other might be measured using the NEO-PI and Minnesota Multiphasic personality Inventory (MMPI) (115 to 118, and 120, 122, 124)) or similar instrument. The measurements to assess depression severity and symptom profile could include the Montgomery Asberg (MA) and Beck Depression (BD) scales, while anxiety could be measured using the Spielberger State Trait Anxiety Index (STAI) or similar instruments.

In the case of a mental or psychiatric illness, these clinical variables are combined with the features extracted from the EEG. This approach differentiates the disclosed method from the method of U.S. Pat. No. 7,177,675 (Suffin) which emphasizes that the EEG data alone are sufficient for prediction of anti-depressant response. In our early studies an improvement of 4% was found in average performance simply by including some very basic clinical information such as the scores on the Beck depression rating scales. Methods of efficiently reducing the feature set in combination with modern mathematically-based classifier and predictor structures and models are provided by the present invention.

Various instruments and methods of medical imaging can be used as part of clinical and laboratory data. For example, in the case of mental and psychiatric illnesses and disorders, although the EEG is currently the mainstay of the brain activity measurement system in the described invention other technologies such as fMRI, MEG, positron emission tomography (PET), single photon emission computerized tomography (SPECT), MRI, magnetic resonance spectrometry (MRS), radiography, and various other medical imaging instruments and probes could also be used. The brain activity data derived from these methods could also be employed in addition to or instead of the data derived from the EEG.

For example, for psychiatric and mental illnesses and disorders, the data of fMRI can be used. There are at least two reasons for using the fMRI: 1) the fMRI and EEG are complementary methods for the analysis of brain activity. The spatial resolution is in the range of millimeters with fMRI and the time resolution is in the range of milliseconds with EEG. Combining the two approaches will therefore yield a more complete assessment of brain activity than what is available with either method used in isolation, 2) During the update and improvement stage of the medical digital expert system, combining fMRI and EEG may help in identifying better features than those which can be extracted using the EEG alone. Ancillary techniques such as mood induction may further enhance predictive power of our method as these strategies may increase the probability that the brain regions activated during the fMRI scan are related to mood disorder, and not to extraneous and random variables or interferences.

Laboratory tests such as biochemistry and hematology could in some instances be an important tool in determining optimal treatment. For example undiagnosed medical illnesses such as anemia, vitamin deficiency, undetected thyroid or liver disease could not only mimic the symptoms of some psychiatric and neurological illnesses, but could also influence the absorption, metabolism and volume of distribution of some medications. Pharmacogenetic data and genetic tests e.g. to determine a persons allelic subtype for the serotonin transporter gene and other genotypes such as the alleles of apolipoprotein E gene may help to divide psychiatric illnesses such as major depression and Alzheimer's into subtypes with different treatment response profiles and prognosis. Adding these variables into the predictive algorithm may increase its predictive power (118, 119).

The utility of the invention has been demonstrated in a variety of experiments in predicting patient responses to a subset of treatments available to the clinician. Another set of experimental data are described using EEG data to differentiate persons with or without various psychiatric diagnoses. In these examples, the predictions are based on EEG measurements alone or in conjunction with a few simple clinical variables in carefully diagnosed research subjects. Unlike previous approaches, of the present invention uses machine learning methods with an EEG database gathered over many years by psychiatrists. The aggregate success rate of the predictions of treatment response is over 85%. The aggregate success rate of the estimations of diagnosis is similar. These encouraging results using such simple information demonstrate considerably improved performance over previous methods.

Other improvements include using advanced signal processing and expert decision systems/procedures, and improved feature extraction techniques. In the algorithms used in the present invention, various forms of medical, clinical and laboratory information, auditory evoked potentials data, event-related potentials, various mood induction or stimulus-driven data, indicators relating to personality and quality of life, family histories, physical characteristics, etc. can be included as part of the information collected to assist in improved prediction. Using statistical and hierarchical decision techniques, and a data fusion expert system, the preliminary results from traditional simple decision systems can be optimally combined and, by calculating an overall final decision with confidence measures, to provide an improved prediction/estimation efficiency. To date, the method and system has been successfully used to predict response to such biologically diverse treatments as antidepressant medication, antipsychotic medication and rTMS. The method has also been used to differentiate persons with major depression from those with schizophrenia and healthy individuals from both of these ill groups.

Detailed Experimental Results

A few example experiments are now discussed in brief (a detailed discussion of the experiments conducted and results obtained follows hereafter).

rTMS is a noninvasive method to excite neurons in the brain and is a form of non-medication treatment for MDD. The excitation is caused by weak electric currents induced in the specific parts of brain tissue by rapidly changing high-intensity magnetic fields (electromagnetic induction). This way, brain activity can be triggered or modulated without the need for surgery or external electrodes. Typically, a period of 2 to 4 weeks of application of TMS is required before the patient experiences relief from depression. rTMS therapy can be considered as a noninvasive version of electroconvulsive therapy (ECT).

In our experiments, we also tested the use of the expert system to predict the likelihood of response to clozapine (by estimating residual symptomatic scores) in patients with Schizophrenia. For Schizophrenia and Schizoaffective disorder, a major component of treatment is pharmacological, including antipsychotics such as clozapine as well as mood stabilizers and antidepressant medications. Clozapine is particularly effective in patients with Schizophrenia and Schizoaffective disorder who have failed trials of other antipsychotic medications. However, clozapine carries an approximately 1% risk of producing life threatening white blood cell suppression. Significant adverse metabolic effects such as elevation of trigyceride levels, weight gain and increased likelihood of developing diabetes are much more common. There is currently no accepted method of determining potential response to clozapine short of an actual clinical trial. Our proposed expert system shows significant performance in predicting the response of Schizophrenic patients to this drug.

As alluded to earlier, the psychiatrist currently has few predictive quantitative techniques for assessing an appropriate treatment for a patient with a psychiatric disorder. The proposed expert system and prediction methodology will significantly improve the likelihood of correct treatment prescription in the first instance, thus avoiding the inefficient trial-and-error process that often characterizes the management of the non-responsive patient.

The treatments considered are selective serotonin reuptake inhibitor (SSRI) anti-depressant drugs, rTMS to treat MDD, and the drug Clozapine for treating schizophrenia. Using current methods, remission rates with treatment for these conditions are disappointingly low ranging from 28 to 42%. The psychiatrist currently does not have access to any quantitative technique for determining an appropriate treatment for a patient with a psychiatric disorder. The expert system and prediction methodology disclosed herein significantly improves the likelihood of correct treatment determination in the first instance, thus avoiding the inefficient trial-and-error process that often characterizes the management of the non-responsive patient.

In patients with MDD, resting EEG signals were measured after 10 days medication withdrawal and before any subsequent antidepressant treatment. The patients with MDD were then randomly assigned to receive 6 weeks of either SSRI plus sham TMS or SSRI plus true TMS. In patients with Schizophrenia the EEG data were collected prior to initiation of new treatment, however, for clinical reasons, they did not have a complete 'drug washout' before recording the EEG. At most six EEG files were collected for each subject/patient: at most 3 EEG files recorded in eyes-open (EO) case, and at most 3 others in eyes-closed (EC) case. The EEG measurements were recorded using a general-purpose and standard EEG system with 16 channels (out of 20) using the standard 10-20 system with linked ears reference and sampling frequency of 205 Hz. Out of 20, four center-scalp EEG sensors (FZ, CZ, PZ, OZ) were not used. Each recorded EEG file was approximately of 3.5 minutes duration and was automatically de-artifacted (to eliminate high-amplitude and highly noisy epochs) and low-pass filtered with a cut-off frequency of 46 Hz.

The initial feature set used in these experiments included some simple quantities such as coherence between all sensor pairs in various frequencies, mutual information between sensor pairs, wavelet analysis coefficients, linear predictive coding (LPC) model and autoregressive model (AR) coefficients, absolute and relative spectrum power levels in various frequency bands, the ratio of left-to-right hemisphere, and the anterior/posterior power gradient at various frequencies and between various sensor pairs. However, as discussed above, only a very small number of N most relevant features are used to construct the prediction models. Furthermore, it is to be noted that the list of discriminating features is not unique. In checking the performance of treatment-efficacy predictors, data of one subject is considered as test data, and data of the rest of subjects are used as training data.

Table 1 gives the performance histogram of our predictions of response to SSRI therapy, based on a sample of 22 subjects with MDD, for EEGs taken when the subject's eyes were closed or open. "Response" was defined as at least a 25% improvement in the Hamilton depression rating score after a period of six weeks of treatment. In this sample the average performance is 100% correct prediction. For each patient, average of prediction values for all available eyes-open and eyes-closed sessions of EEG recordings are used as the final treatment-response prediction result.

TABLE 1

Performance results for predicting the response to SSRI in patients with MDD.

| | predicted non-responders | predicted responders | % correct |
|---|---|---|---|
| true non-responders | 14 | 0 | 100% = specificity |
| true responders | 0 | 8 | 100% = sensitivity |

Similarly, the performance histogram for prediction of response to the rTMS therapy for 41 subjects is shown in Table 2. The average performance is 90.5%. It is possible to predict the response to TMS therapy using either EO or EC EEG data, or both.

TABLE 2

Performance results for predicting the response to rTMS in patients with MDD.

| | predicted non-responders | predicted responders | % correct |
|---|---|---|---|
| true non-responders | 19 | 3 | 86.36% = specificity |
| true responders | 1 | 18 | 94.74% = sensitivity |

Table 3 shows the performance histogram of predictions for response to Clozapine therapy, for 23 Schizophrenic subjects. Subjects were divided into "responders" and "non-responders" based on whether the overall Schizophrenic symptoms score fell above or below a threshold (which is a score close to the median value). The overall score used, was the 'total-rank' (TR) which is sum of three scores: general rank (GR), positive (or productive) symptoms scale (PSS), and negative (or deficit) symptoms scale (NSS), based on post-treatment "positive and negative symptoms scale" (PANSS). The average performance is 100% correct prediction. Approximately similar performance was obtained in other experiments using 'global assessment of functioning' (GAF), as the response-indicator variable.

TABLE 3

Performance results for predicting the response to drug Clozapine in Schizophrenic patients.

| | predicted non-responders | predicted responders | % correct |
|---|---|---|---|
| true non-responders | 12 | 0 | 100% = specificity |
| true responders | 0 | 11 | 100% = sensitivity |

Though the foregoing examples have focused on the treatment of MDD and schizophrenia, the basic principles described (i.e. baseline QEEG data alone or together with a variety of clinical, historical, psychological, cognitive and biological assessment variables and analyzing these in the described manner in relation to outcome after specified treatment has been applied) can be applied to any of a number of psychiatric and neurological illnesses, as well as to any other illness or abnormality.

As mentioned earlier, the data collection and analysis methods, and machine learning and inference procedures of the invention can also be used for diagnosis. This has been demonstrated through differentiation of patients previously diagnosed with MDD or schizophrenia versus normal (healthy) individuals. The diagnosis experiments were conducted using only EEG measurements in carefully diagnosed research subjects. The study sample consists of 195 subjects, including 64 patients with MDD, 40 Schizophrenic patients and 91 healthy (or normal) subjects. The subjects with MDD or Schizophrenia were carefully diagnosed using the "American Psychiatric Association's Diagnostic and Statistical Manual" (DSM) criteria by experienced psychiatrists specializing in the management of either mood disorders or Schizophrenia. In most subjects with MDD, the diagnosis was confirmed using the Structured Clinical Interview for DSM. Therefore, clinical diagnosis (used as our reference and training data in machine learning procedure) is done with high accuracy. In patients with MDD, resting EEG signals are measured after 10 days medication withdrawal and before any subsequent treatment is started (i.e., they correspond to pre-treatment or baseline stage). In patients with Schizophrenia the EEG data are collected prior to initiation of new treatment, however, for clinical reasons, they do not have complete 'drug washout' before recording the EEG. The parameters and experimental setup were similar to the ones discussed before in the 'treatment-efficacy prediction' experiment.

All recorded eyes-open and eyes-closed EEG data are used collectively, and the diagnostic performance is tested using physician's diagnosis as our "reference", or "true" value. The diagnosis outcome for each patient reflects the average of estimation results for all eyes-open and eyes-closed data that were available. Table 4 shows the result when the 42 simple relevant features (selected based on mutual information) are used to construct the medical diagnosis model. The diagnosis performance is above 87.5% in all cases. While in most cases, differentiating MDD from Schizophrenia is not clinically difficult there are many common symptoms between these two types of mental disorder, and diagnostic confusion can occur, particularly with psychotic MDD, or partially treated schizophrenia with prominent negative (depressive-like) symptoms.

TABLE 4

Three-class diagnosis performance results for estimating/detecting the type of illness/condition.

| | Estimated to have MDD | Estimated to have Schizophrenia | Estimated to be normal (or healthy) |
|---|---|---|---|
| Clinically diagnosed as MDD | 56 (87.5%) | 8 | 0 |
| Clinically diagnosed as Schizophrenic | 2 | 36 (90%) | 2 |
| Normal (or healthy) | 1 | 9 | 81 (89%) average performance = 88.8% |

In the above example a two-class diagnosis scenario was also investigated using pre-treatment EEG to differentiate normal (healthy) subjects from patients who suffer from either MDD or Schizophrenia. Table 5 reflects the diagnosis performance using 14 simple relevant features. The cognitive diagnosis system made 9 errors out of a total of 195 subjects, and the average performance is 95.2%. From the group of subjects with mental disorder (MDD or Schizophrenia), all 3 misdiagnosed by the cognitive system are among those clinically diagnosed by physician as Schizophrenic.

TABLE 5

Diagnosis performance results for differentiating healthy subjects from patients with mental disorders (who have either MDD or Schizophrenia).

|  | Estimated to have either MDD or Schizophrenia | Estimated to be normal (or healthy) | total |
|---|---|---|---|
| Clinically diagnosed as MDD or Schizophrenic | 101 (97.1%) | 3 | 104 |
| Normal (or healthy) | 6 | 85 (93.4%) | 91 |
|  |  | average performance = 95.2% | 195 |

In a similar example, a two-class diagnosis to differentiate depressed patients (with MDD) from Schizophrenic patients (using only pre-treatment EEG) is also tested. Table 6 reflects the diagnosis performance using 14 simple relevant EEG features selected from those extracted. There are a total of 104 subjects participated in this experiment: 64 patients with MDD and 40 patients with Schizophrenia. There were 10 misdiagnosed cases. The explanation for this is unclear.

TABLE 6

Diagnosis performance results for recognizing depressed patients (with MDD) from patients with Schizophrenia, using pre-treatment EEG information.

|  | Estimated to have MDD | Estimated to be Schizophrenic | total |
|---|---|---|---|
| Clinically diagnosed as depressed (MDD) | 58 (90.62%) | 6 | 64 |
| Clinically diagnosed as Schizophrenic | 4 | 36 (90%) | 40 |
|  |  | Average performance = 90.3% | 104 |

Further Experimental Details

In addition to EEG, or QEEG information, clinical and symptomatic scaling are also found to be relatively useful. For decades, researchers have attempted to identify clinical predictors of antidepressant response to medication and psychotherapy. Well-articulated theoretical models have been advanced to describe how personality factors interact with the onset, maintenance, and treatment of depression.

In addition, a considerable body of evidence suggests that the personality trait of neuroticism increases the probability of a poor outcome in depression. Our data indicate that adding some syndromatic information, specifically basic depression rating scale scores derived from questions related to different depressive symptoms, to our algorithm increases the prediction performance beyond that seen using EEG measures alone.

In the following analyses of data derived from TMS and SSRI experiments, we added clinical (specifically some simple symptomatic) attributes to the EEG data. The clinical data used, when available, are symptom rating scales, the "Hamilton depression rating scale" (HamD) an observer-reported scale and the "Beck depression inventory" (BDI), a self-report rating scale.

We found that the prediction performance by using SVR and Kernel PLSR methods are approximately equivalent. The continuous values obtained by these methods are quantized to discrete decision values, i.e. $y_i$ is assigned a value of "1" if patient i is non-responsive to the treatment (denoted NR), and a "2" if the patient is responsive (denoted R). After finding the classification function $f(x)$, a decision threshold of 1.5 is used. This means, for example, that if $f(x_i)>1.5$, then patient i is estimated to be "responsive" to the treatment.

In our analysis, for each patient, we have several epochs of data. Despite the fact that the EEG data has different characteristics in the EO versus EC case, our predictors (based on the larger collection of all EO and EC data) were able to find common discriminative features for the two sets. There are 6 EEG data collections for each patient (3 EO plus 3 EC, if available), and our final treatment-response prediction result for each patient is based on averaging the corresponding points in the feature space before a decision is made.

In our experiments, we also tested the prediction performance using only EO data, or using only EC data. In either of these experiments, the number of data epochs is less than the experiment when all available EO and EC are used together. However, the average treatment-efficacy prediction performance was similar in all experiments.

A. SSRI Therapy

In our SSRI therapy experiment, the available data correspond to 14 non-responder, and 8 responder patients, and the prediction performance obtained from our methodology is 100%, when using $N_f=12$ most relevant features.

Figure 9:
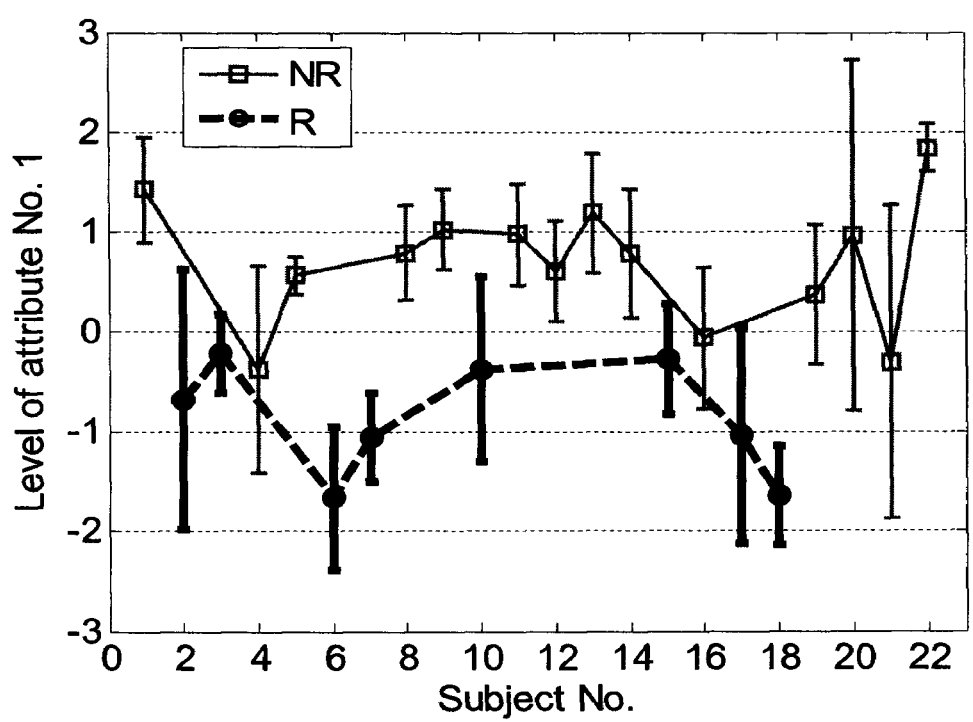
FIG. 9 shows a comparison of attribute number 1 among responders versus non-responders to SSRI therapy. The attribute is: 'Coherence at 10 Hz, for EEG sensor pair T3-T5'.

In SSRI experiment, for example, each single simple feature in the list of 12 best that we used has some relevance to the prediction problem; however, it is the overall joint information hidden in collective data of all these 12 simple features that allow us to obtain high prediction performance. As an example, particularly with regard to SSRI response prediction, feature number 1 (Coherence at 10 Hz between EEG sensor pair T3-T5) may be seen to have a relatively good discriminative power. See FIG. 9 which shows the average level of this feature for each patient and compares responders versus non-responders, where the standard deviation is shown using error-bars. The average z-score value of this attribute for responders and non-responders are −0.86 and 0.7, respectively, and therefore this feature alone is already a good discriminator (with some uncertainly, however). The error-bar shows the standard deviation calculated from all the EEG data epochs belonging to each patient.

Figure 10:
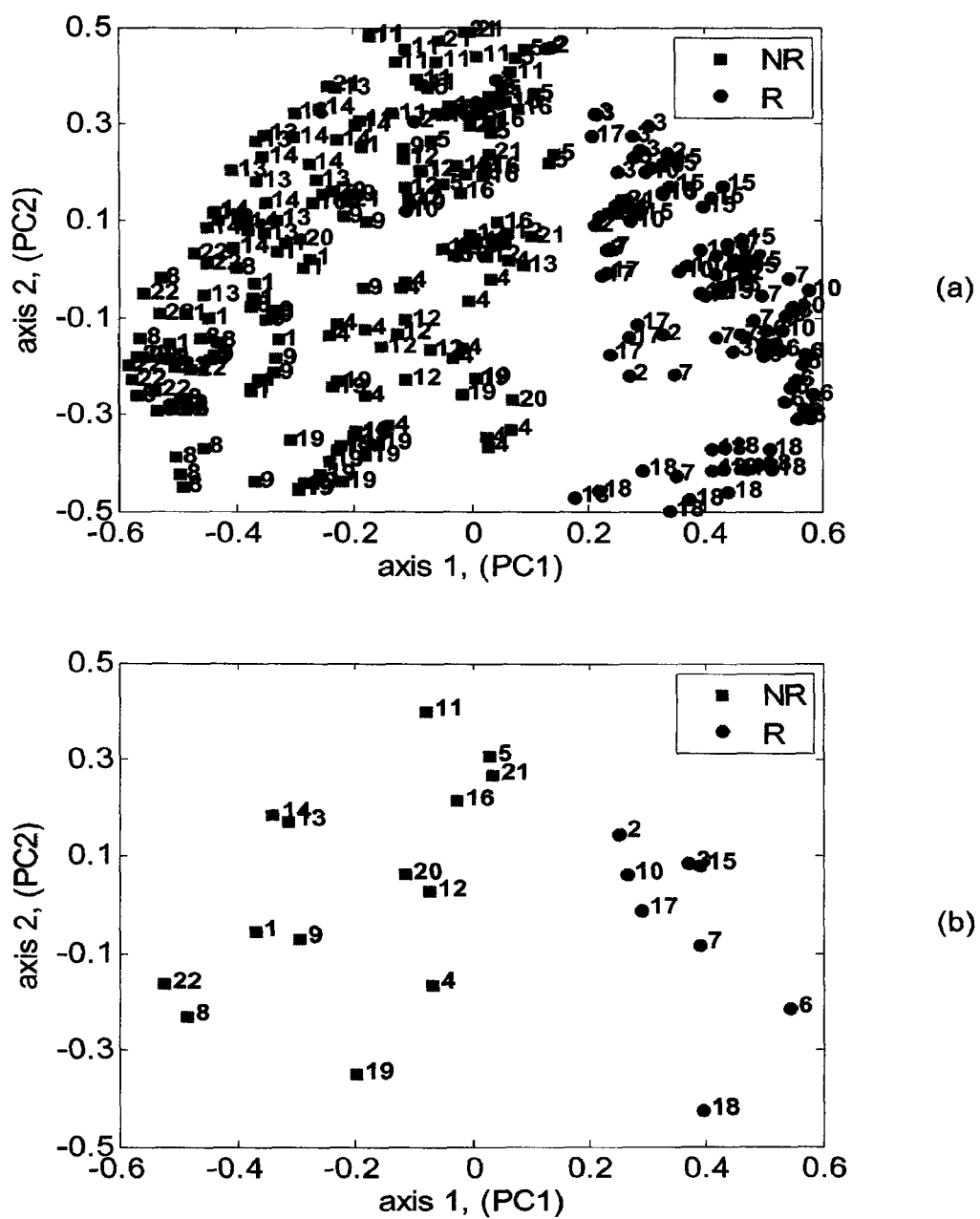
FIG. 10 relates to SSRI therapy and shows a scatter plot of projection of pre-treatment data samples onto the first 2 major principal components using the KPCA method with a Gaussian kernel. 'NR' denotes subjects who are non-responsive to SSRI (after 6 weeks of treatment), and 'R' denotes responsive subjects.

FIG. 10.a shows the scatter plot of the 294 points corresponding to 294 epochs of data (collections of eyes-open sessions and eyes-closed sessions of pre-treatment EEG recording) of 22 subjects using KPCA method with a Gaussian kernel. It shows noticeable geometric separation and clustering of attributes of the subjects into two classes. FIG. 10 corresponds to the projection of data samples onto the first and second major principal components. In this figure, each subject has a number of data epochs, and the patient index is written beside each data sample. Averaging the location of projected data samples belonging to each subject results in FIG. 10.b, in which each subject is shown with only one point.

For a new test data, one can calculate its projection onto these figures. Then, the physician can use this kind of visual display, and look at the location of projected test sample to approximately find out whether the test patient is similar to responders or to non-responders.

Note that FIG. 10 represents the data projected onto only 2 nonlinear principle component dimensions. This is done for the purposes of visualization only, to show the clustering behaviour of responding vs. non-responding patients. The clustering behaviour is indeed very evident, as verified by the figures. In performing the actual classification task, all 12 best features (dimensions) would be used.

The effect of clinical depression rating scales on prediction performance was also determined. For SSRI therapy response prediction, using only eyes-open EEG data set and among the 12 best discriminating attributes, the following three clinical ratings are found to be relevant: (i). "HamD12: Insomnia Middle", (ii). "Bk5: Feeling of Guilt", (iii). "HamD19: Anxiety Psychic" scores.

B. TMS therapy

Figure 11:
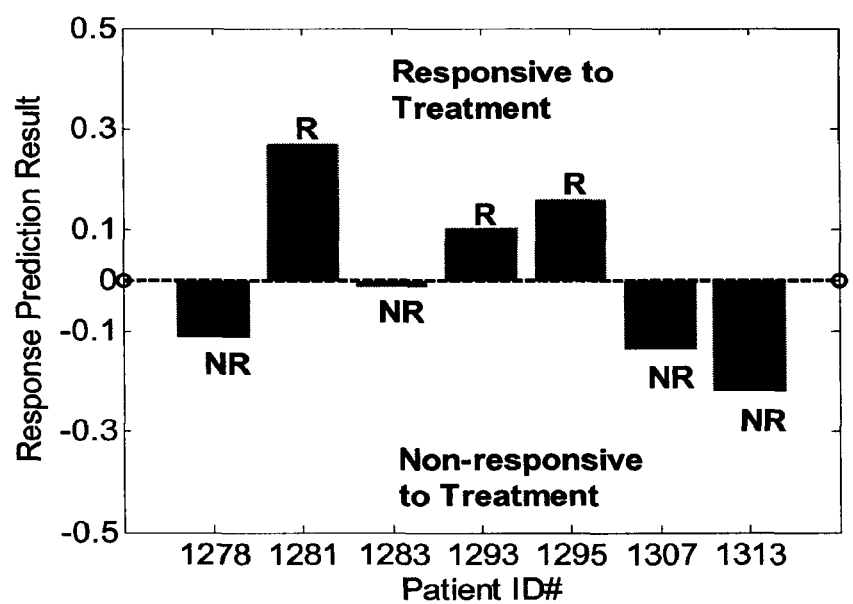
FIG. 11 illustrates an independent experimental test for TMS response prediction and provides an illustrative example of one type of prediction result on 7 new test subjects, using both EO and EC pre-treatment data.

When using only eyes-closed EEG data, in another clinical experiment, a comparison among different prediction/classification techniques is shown in Table 7. It shows that in this particular experiment, SVR and KPLSR methods with a Gaussian kernel are among the best models with 91% prediction performance, however, the 'mixture of factor analysis' (MFA) methods are the best in this experiment. The MFA-1 model used in the experiment has 1 mixture component with 4 factors resulting in average performance of 94.12%. The MFA-2 model used in the experiment has 4 mixture components with 2 factors resulting in average performance of 96.87%. Using a grid search, the best parameters for each method are found, and Table 7 reflects the best performance attainable with each technique. For example, a polynomial kernel of degree 8 is used with the support vector machine (SVM) technique. The k-nearest-neighbor (kNN), least-squares (LS), and linear discriminant analysis (LDA) methods are other standard classification techniques used as references in our comparison, S. Theodoridis and K. Koutroumbas, *Pattern Recognition*, $2^{nd}$ ed. USA: Elsevier Academic Press, 2003. The regularized least squares (RLS) regression technique is based on a two-term regularization problem with $L(y, f(x;\Theta)) = \|y_i - f(x_i)\|_2^2$ and uses Gaussian kernels to construct the prediction function. See S. Haykin, *Neural Networks, A Comprehensive Foundation*, $2^{nd}$ ed. Prentice Hall, 1999 and T. Evgeniou, M. Pontil, and T. Poggio, *Regularization networks and support vector machines*, Advances in Computational Mathematics, vol. 13, no. 1, pp. 1 to 50, April 2000.

using pre-treatment data of 35 subjects (who received TMS treatment), and then tested another independent set of 7 patients who were not included in the training set. The response-prediction result is shown in FIG. 11, using the SVR method with a linear kernel. The predictor result, (y), is subtracted from 1.5, to obtain this display. The positive vertical values correspond to the subject being responsive to treatment. Here, zero is the decision threshold and is shown with a dashed line. Subject 1283, whose result is close to the decision boundary, is slightly similar to non-responders; however, in clinical practice, it might be better to recommend TMS therapy to this patient, with the hope that he/she might respond. Therefore, the clinician can change the decision threshold to be on the safe side. In this test, based on the clinical records, the response prediction result confirms correctly with the clinical assessment after 6 weeks of therapy, and therefore this shows that our prediction methodology is indeed successful.

Clozapine Therapy

In Schizophrenic patients participated in the experiment, we also measured treatment efficacy using 'global assessment of functioning' (GAF) score measured post-treatment. Using pre-treatment EEG data, in an experiment, the level of post-treatment GAF was predicted. The two levels (or classes) are 1. 'seriously ill or with impairment': GAF <41.5, NR'.

This corresponds to being non-responsive (NR) to clozapine therapy.

2. 'functional, and with less severe symptoms': GAF >=41.5, 'R'.

This corresponds to being responsive (R) to clozapine therapy.

With 23 Schizophrenic patients, treatment efficacy prediction performance based on 'total-rank' (TR) with $\delta=88.5$ was 100%. The same performance is obtained when 'nega-

TABLE 7

Comparison of performance among different methods in predicting the response to TMS therapy, using only 'eye-closed' data recording plus 'Bk13'. 33 depressed subjects are involved in the study. $N_i = 14$.

| Method | Specificity, $p(\hat{y} = 1|y = 1)$ | Sensitivity, $p(\hat{y} = 2|y = 2)$ | % average performance |
|---|---|---|---|
| LDA | 76.47 | 87.5 | 81.99% |
| K-Nearest Neighbour | 76.47 | 81.25 | 78.86% |
| Least Squares (LS) | 76.47 | 81.25 | 78.86% |
| RLS | 82.35 | 93.75 | 88.05% |
| SVR with linear kernel | 82.35 | 87.5 | 84.93% |
| SVM with polynomial kernel | 88.24 | 81.25 | 84.74% |
| SVR with Gaussian kernel | 88.24 | 93.75 | 91% |
| PLSR with Gaussian kernel | 88.24 | 93.75 | 91% |
| Mixture of Factor Analysis, model MFA-1 | 88.24 | 100 | 94.12 |
| Mixture of Factor Analysis, model MFA-2 | 100 | 93.75 | 96.87 |
| Radial Basis Network (RBN) | 76.47 | 87.5 | 81.98 |
| Multilayer Perceptron (an artificial neural network model) | 76.47 | 81.25 | 78.86 |

In Table 7, among the $N_i$ features used, one of them is not derived from EEG information, but instead it is a particular clinical depression rating score. With the simple feature ranking based on 'minimum redundancy criterion', it is noted that the "Bk13: Indecision" score was relevant and added this to EEG-based attributes to build the prediction model. "Bk13" is one of the scores in the "Beck depression inventory" (BDI) derived from questions related to different depressive symptoms.

As an illustrative example, another independent experimental test, was conducted in which the predictor is trained tive symptoms scale' (NSS) with $\delta=23.5$ is used as target variable to recognize responders versus non-responders. Best of $N_i=14$, or $N_i=12$ is used. Based on GAF score, the average performance is 91.15%. Based on PSS scale with decision threshold $\delta=17.5$, the performance was 95.83%.

Figure 12:
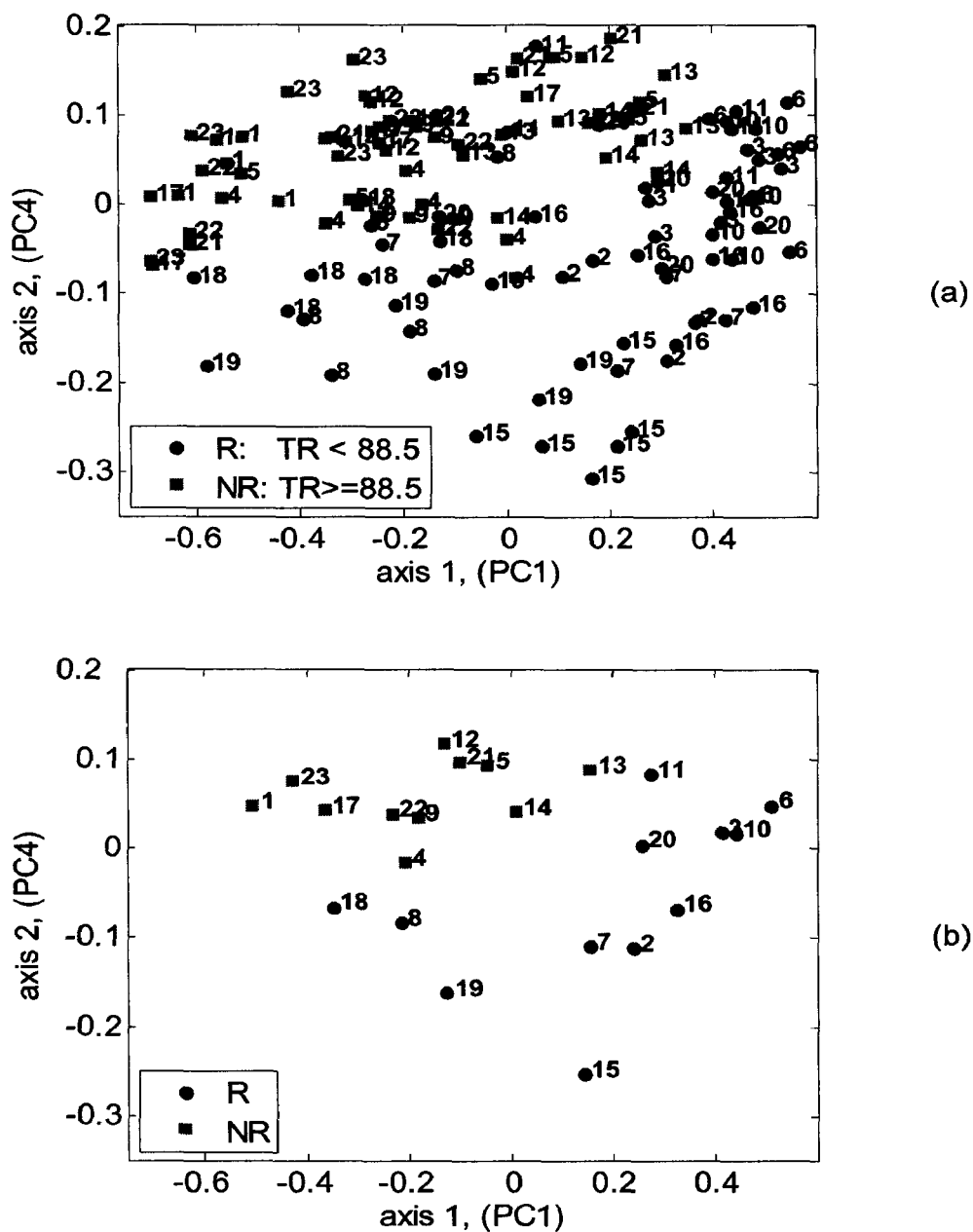
FIG. 12 relates to post-treatment 'total-rank' (TR) schizophrenic symptoms score level prediction and is a scatter plot of projection of pre-treatment data (epochs) into PC1 and PC4.

When taking TR as the target variable, FIG. 12.a shows the scatter plot of pre-treatment EEG data (including 135 epochs) using KPCA with Gaussian kernel into two major principal components, (PC1 and PC4). Depiction using two-dimensional space cannot optimally demonstrate clear separation of the two classes of patients, nonetheless noticeable geometric separation and clustering of attributes of the subjects into two classes is evident. The PC numbers are selected based on having maximum mutual information with target variable.

Averaging the location of projected data samples belonging to each subject results in FIG. 12.b, in which each subject is shown only with one point. FIG. 12.b shows a subject-wise scatter-plot of projected data in clozapine therapy, based on post-treatment 'total-rank' (TR) level. 'R' corresponds to TR<88.5, and 'NR' corresponds to TR>=88.5.

Figure 13:
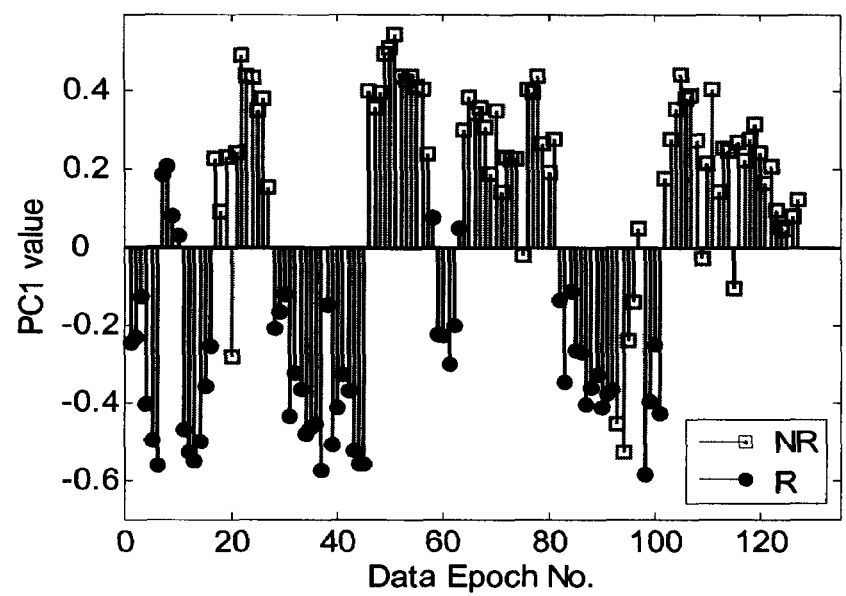
FIG. 13 shows a scatter plot of projection of pre-treatment data (epochs) into the major principal component in clozapine treatment efficacy prediction. 'R' corresponds GAF>=41.5 (filled circles), and 'NR' corresponds to GAF<41.5 (rectangles).

With GAF as target variable, we noted that using KPCA method using Gaussian kernel, the first major principal component has good discrimination capability. There are however, a few overlapping points in this one-dimensional plot. See FIG. 13, which shows a scatter plot of projection of pre-treatment data (epochs) into the major principal component. 'R' corresponds GAF >=41.5 (filled circles), and 'NR' corresponds to GAF <41.5 (rectangles).

Diagnosis

Figure 14:
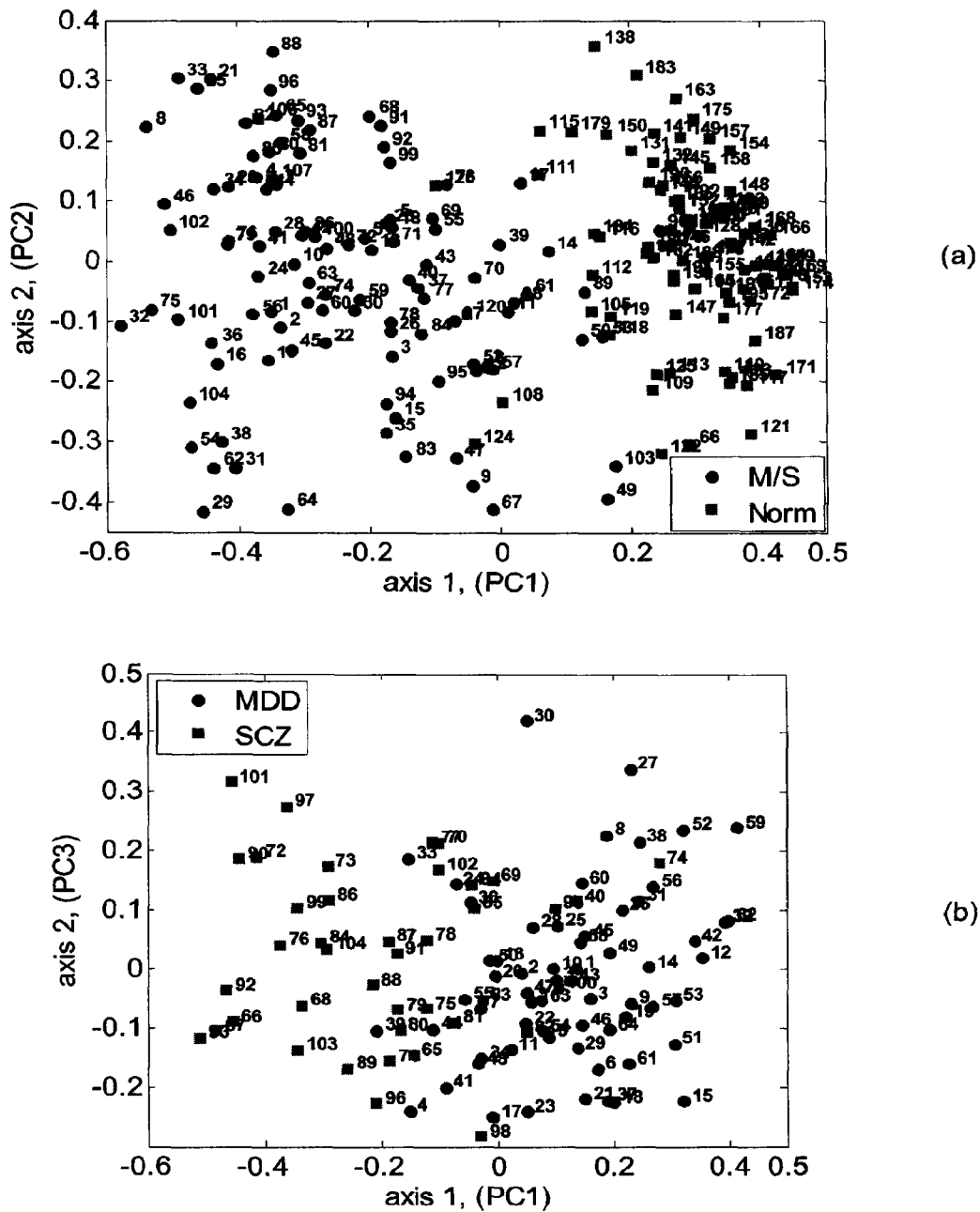
FIG. 14 shows a scatter plot of projection of data samples (subject-wise) into two major principal components.

FIG. 14 shows a scatter plot of projection of pre-treatment data (subject-wise) into two major principal components. In FIG. 14.a, 'M/S' corresponds to 'MDD or Schizophrenia' subjects (filled circles), and 'Norm' corresponds to normal or healthy subjects (rectangles). FIG. 14.a shows that baseline EEG data gives approximately enough information in separating these two classes. In FIG. 14.b shows that baseline EEG data gives valuable information in approximately separating MDD patients from Schizophrenic patients.

Though the foregoing examples have focused on mental and psychiatric disorders and illnesses, and particularly on the diagnosis of MDD and Schizophrenia, the basic principles described (i.e. using EEG alone or in combination with a variety of clinical, laboratory, physical, historical, psychological, cognitive and biological assessment information and variables and analyzing these in the described manner) can be applied to any of a number of other types of diseases or conditions.

The report regarding treatment response/efficacy prediction, the diagnosis report, and also the related estimation/detection results provided by the medical digital expert system, can have various forms and formats. This includes a variety of graphic formats and waveforms, various graphic representations and plots, continuous decision/estimation/prediction values, multi-level and discrete decision/estimation/prediction values and numbers, etc., and combinations thereof. For example, one option for reporting the treatment recommendation is to a two-level report (saying, either the patient is likely to be "responsive", or "non-responsive" to a therapy), while a three-level report can say that the patient is either "sensitive/responsive", "intermediate/unsure", or "insensitive/nonresponsive" to a particular therapy. The medical digital expert system can also be used to predict whether a patient is likely to respond to a therapy, by providing a likelihood or response-indicator number (that can be either discrete or continuous).

The system and methods of the present invention can be used to predict the response to medication and other forms of treatment. This analytic method allows the user to subdivide patients meeting diagnostic criteria for a particular illness into subgroups with preferential response to a particular form or forms of treatment. Optionally, this method can be adapted to provide guidance regarding diagnosis. Permitting the clinician to confirm his or her diagnostic impressions, or to be informed of other diagnostic possibilities that might be considered. The present invention eliminates much of the uncertainty inherent in current clinical practice and would represent a significant advance in clinical management. In another embodiment of the system and methodology, the medical digital expert system, is used for early diagnosis or to detect vulnerability or increased risk of developing any illness or condition including any psychiatric, neurological or medical illness, disorder or condition in those who have not yet demonstrated easily detectable symptoms of that illness, disorder or condition.

The above disclosure generally describes the present invention so that one of ordinary skill in the art can implement the methods of the present invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference.

Although the preceding description of the invention is in the context of the embodiments and examples described herein, the embodiments are not intended to be a limitation on the scope and application of the invention. As readily recognized by those skilled in the art, the disclosed invention encompasses the disclosed idea and embodiments along with other embodiments providing alterations and modifications to any part of the system and methodology including variations on communications, data transfer and interface subsystems and equipment, choice and design of data management software and subsystems, choice and design of data security methods and subsystems, choice and design of information processing and analysis equipments and methods, choice and design of data acquisition subsystems and equipments, choice and design of machine learning and inference methods, choice and design of signal and information processing methods and computational models, choice and design of discriminative and indicative attributes, features and information, choice and design of prediction and estimation methods, choice and design of feature extraction and feature selection methods, choice and design of classification, recognition, clustering and low-dimensional representation methods and strategies, choice and design of data fusion strategies and methods, choice and design of rule-based, fuzzy learning and inference methods and strategies, choice and design of fuzzy network learning and inference methods, choice and design of hierarchical, multi-level and structural learning and inference methods and strategies, choice and design of feedback procedures, adaptive learning, gradual improvement and revision methods and procedures, choice and design of interface, software, hardware and remote treatment-recommendation implementations and the like without departing from the form, scope and spirit of the invention and teaching disclosed herein.

The invention claimed is:

1. A computer-implemented method for predicting patient response to treatment for a subject patient, the method comprising:
   receiving, for a subject patient, a subject patient dataset including features obtained for a reduced feature dataset; and
   comparing the subject patient dataset to a feature data scheme to predict a response for the subject patient;
   wherein the feature data scheme comprises:
   (a) a diagnostic model for determining a diagnosis of one of a plurality of known disorders indicated by an individual patient dataset; and
   (b) a plurality of diagnosis-specific treatment response models, each of the diagnosis-specific treatment response models corresponding to a specific diagnosis of one of the known disorders, the treatment response models configured to use feature data to predict treatment response;

wherein comparing the subject patient dataset to the feature data scheme to predict the response for the subject patient comprises:

applying the diagnostic model to the subject patient dataset to determine a subject patient diagnosis of one of the known disorders indicated for the subject patient by the subject patient dataset; and selecting and applying one of the diagnosis-specific treatment response models to the subject patient dataset to predict the response for the subject patient;

wherein the selected diagnosis-specific treatment response model corresponds to the determined subject patient diagnosis.

2. The method of claim 1, wherein comparing the subject patient dataset to the feature data scheme to predict the response for the subject patient is carried out on-site where the subject patient dataset is collected.

3. The method of claim 1, wherein:

the subject patient dataset is received at a central processing site remote from a site where the subject patient dataset is collected; and comparing the subject patient dataset to the feature data scheme to predict the response for the subject patient is carried out at the central processing site.

4. The method of claim 1, wherein the feature data scheme comprises:

a plurality of predictor architectures, each predictor architecture independently producing a preliminary treatment response prediction given the measured patient related data; and a data fusion architecture for combining the preliminary treatment response predictions.

5. The method of claim 1, wherein the feature data scheme is generated by:

storing, on a system database, a first level training dataset comprising a plurality of records comprising measured patient related data from a large number of patients, the measured patient related data including clinical and/or laboratory data, diagnoses of presence or absence of known disorders and data relating to patient treatment response;

processing the measured patient related data to extract features from the measured patient related data to generate an extracted feature dataset;

processing the extracted feature dataset to derive the feature data scheme;

the feature data scheme including the reduced feature dataset whose cardinality is less than that of the extracted feature dataset;

the reduced feature dataset being derived by processing the data to obtain features appearing to discriminate for a useful prediction.

6. A method according to claim 5, wherein processing the extracted feature dataset includes segregating the feature data to discriminate for treatment response.

7. A method according to claim 5, wherein the feature data scheme allocates feature data values to a treatment response category.

8. A method according to claim 5, wherein the feature data scheme is determined by solving a multi-dimensional or joint optimization problem, according to a criterion of optimality.

9. A method according to claim 8, wherein the optimization problem is constrained by one of model accuracy and model structure.

10. A method according to claim 5, wherein the feature data scheme is derived by defining one or more decision or estimation functions between feature data values to segregate or discriminate between response categories.

11. A method according to claim 5, wherein processing the extracted feature dataset to derive the feature data scheme comprises defining one or more non-linear boundaries between feature data values.

12. A method according to claim 5, wherein processing the extracted feature dataset comprises processing according to a criterion of optimality.

13. A method according to claim 5, wherein one or more of the clinical and/or laboratory data are derived by means of a brain activity or brain structure monitoring system.

14. A method according to claim 5, wherein one or more of the clinical and/or laboratory data are derived by means of an electromagnetic monitoring system.

15. A method according to claim 5 wherein one or more of the clinical and/or laboratory data are derived by means of an EEG system wherein EEG data is derived from the patient(s) prior to undergoing the treatment for which response is being predicted.

16. A method according to claim 5, wherein one or more of the clinical and/or laboratory data relates to one or more of demographic, mood, anxiety or other psychiatric or neurological symptomatology, medical co-morbidity, pharmacological, biochemical, hematological, hepatic, renal, endocrine, immunologic, nutritional, metabolomic, genetic markers, cognitive or personality assessment information derived from the subject patient.

17. A method according to claim 5, wherein processing the extracted feature dataset comprises defining boundaries between feature data values to segregate the values into different classes.

18. A method according to claim 5, wherein a joint or multivariate criterion of optimality is employed to establish a decision and/or regression function to minimize classification and/or modeling error.

19. A method according to claim 5, wherein processing the extracted feature dataset comprises one of kernelization, mapping, linear data transformation and non-linear data transformation.

20. A method according to claim 5, wherein the feature data scheme is refined using a feedback step in which the training dataset is updated with further follow-up training data from patients.

21. A method according to claim 20, wherein the further follow-up training data comprises patient datasets in addition to patient response information.

22. A method according to claim 20, wherein the reduced feature dataset can change in response to updating of the training dataset with the further follow-up training data.

23. A method according to claim 20, wherein follow-up information regarding the response outcome that is determined to be either unreliable or invalid after screening is excluded from further use as part of the updated training data set.

24. A method according to claim 5, wherein processing the extracted feature dataset reduces the number of features to less than 20 from a number of training dataset candidate features in excess of 500.

25. A method according to claim 5, wherein processing the extracted feature dataset utilizes at least one of probabilistic estimation methods, information-theoretic decision or estimation procedure, and graphical network methods, to generate quantitative features or attributes characterizing at least one of statistical, geometrical, temporal, graphical, network, hierarchical or dynamic model properties of the measured data.

26. A method according to claim 5, wherein processing the extracted feature dataset utilizes a maximum mutual information technique.

27. A method according to claim 5, wherein processing the extracted feature dataset includes a procedure for ensuring the reduced feature dataset has minimum mutual redundancy.

28. A method according to claim 5, in which one or more of the clinical and/or laboratory data are derived by means of a brain activity or structure monitoring system, and one or more of the clinical and/or laboratory data elates to biological test results or demographic, mood, anxiety or other psychiatric symptomatology, medical co-morbidity, pharmacological, biochemical, hematological, hepatic, renal, endocrine, immunologic, nutritional, metabolomic, genetic markers, cognitive or personality assessment information derived from the subject patient.

29. A medical system comprising:
a first computer, wherein the first computer comprises:
storage for storing a feature data scheme, wherein the feature data scheme comprises:
(a) a diagnostic model for determining a diagnosis of one of a plurality of known disorders indicated by an individual patient dataset; and
(b) a plurality of diagnosis-specific treatment response models, each of the diagnosis-specific treatment response models corresponding to a specific diagnosis of one of the known disorders, the treatment response models configured to use feature data to predict treatment response; and
at least one processor coupled to the storage and to an input device, the processor executing instructions for:
receiving, for a subject patient, a subject patient dataset including features obtained for a reduced feature dataset; and
comparing the subject patient dataset to a feature data scheme to predict a response for the subject patient;
wherein comparing the subject patient dataset to the feature data scheme to predict the response for the subject patient comprises:
applying the diagnostic model to the subject patient dataset to determine a subject patient diagnosis of one of the known disorders indicated for the subject patient by the subject patient dataset; and
selecting and applying one of the diagnosis-specific treatment response models to the subject patient dataset to predict the response for the subject patient;
and wherein the selected diagnosis-specific treatment response model corresponds to the determined subject patient diagnosis.

30. The medical system of claim 29, wherein the feature data scheme is generated by:
storing, on a system database, a first level training dataset comprising a plurality of records comprising measured patient related data from a large number of patients, the measured patient related data including clinical and/or laboratory data, diagnoses of presence or absence of known disorders and data relating to patient treatment response;
processing the measured patient related data to extract features from the measured patient related data to generate an extracted feature dataset;
processing the extracted feature dataset to derive the feature data scheme;
the feature data scheme including the reduced feature dataset whose cardinality is less than that of the extracted feature dataset;
the reduced feature dataset being derived by processing the data to obtain features appearing to discriminate for a useful prediction.

31. A medical system according to claim 30, wherein the system includes a feedback arrangement in which the training database is updated with further training data to update the feature data scheme.

32. A medical system according to claim 29, further including means for inputting patient derived data.

33. A medical system according to claim 29, further comprising a brain activity or brain structure monitoring device for inputting patient derived feature data wherein the brain derived data is derived from the patient(s) prior to undergoing the treatment for which response is being predicted.

34. A computer-implemented method for assessment of status of a patient, the method comprising:
receiving, for a subject patient, a subject patient dataset including features obtained for a reduced feature dataset; and
comparing the subject patient dataset to a feature data scheme to allocate an assessment status for the subject patient;
wherein the feature data scheme comprises:
(a) a diagnostic model for determining a diagnosis of one of a plurality of known disorders indicated by an individual patient dataset; and
(b) a plurality of diagnosis-specific assessment status models, each of the diagnosis-specific assessment status models corresponding to a specific diagnosis of one of the known disorders, the assessment status models configured to use feature data to allocate an assessment status;
wherein comparing the subject patient dataset to the feature data scheme to allocate the assessment status for the subject patient comprises:
applying the diagnostic model to the subject patient dataset to determine a subject patient diagnosis of one of the known disorders indicated for the subject patient by the subject patient dataset; and
selecting and applying one of the diagnosis-specific assessment status models to the subject patient dataset to allocate the assessment status for the subject patient;
and wherein the selected diagnosis-specific assessment status model corresponds to the determined subject patient diagnosis.

35. The method of claim 34, wherein comparing the subject patient dataset to the feature data scheme to allocate the assessment status for the subject patient is carried out on-site where the subject patient dataset is collected.

36. The method of claim 34, wherein:
the subject patient dataset is received at a central processing site remote from a site where the subject patient dataset is collected; and
comparing the subject patient dataset to the feature data scheme to allocate the assessment status for the subject patient is carried out at the central processing site.

37. The method of claim 34, wherein the feature data scheme comprises:

a plurality of estimator architectures, each estimator architecture independently producing a preliminary assessment allocation given the measured patient related data; and a data fusion architecture for combining the preliminary assessment allocations.

38. The method of claim 34, wherein the feature data scheme is generated by:

storing, on a system database, a first level training dataset comprising a plurality of records comprising measured patient related data from a large number of patients, the measured patient related data including clinical and/or laboratory data and diagnoses of presence or absence of known disorders;

processing the measured patient related data to extract features from the measured patient related data to generate an extracted feature dataset;

processing the extracted feature dataset to derive the feature data scheme;

the feature data scheme including the reduced feature dataset whose cardinality is less than that of the extracted feature dataset;

the reduced feature dataset being derived by processing the data to obtain features appearing to discriminate for a useful prediction.

39. A method according to claim 38, wherein processing the first level training dataset includes segregating the feature data to discriminate between assessment status.

40. A method according to claim 34, wherein the feature data scheme allocates feature data values to an assessment status category.

41. A method according to claim 38, wherein the feature data scheme is derived by defining one or more decision or estimation functions between feature data values to segregate or discriminate between assessment status categories.

42. A method according to claim 38, wherein the feature data scheme is derived by defining one or more non-linear boundaries between feature data values.

43. A method according to claim 38, wherein processing the first level training dataset comprises processing the first level training dataset according to a criterion of optimality.

44. A medical system comprising:

a computer, wherein the computer comprises:

storage for storing a feature data scheme, wherein the feature data scheme comprises:

(a) a diagnostic model for determining a diagnosis of one of a plurality of known disorders indicated by an individual patient dataset; and (b) a plurality of diagnosis-specific assessment status models, each of the diagnosis-specific assessment status models corresponding to a specific diagnosis of one of the known disorders, the assessment status models configured to use feature data to allocate an assessment status;

at least one processor coupled to the storage and to an input device, the processor executing instructions for:

receiving, for a subject patient, a subject patient dataset including features obtained for a reduced feature dataset; and comparing the subject patient dataset to a feature data scheme to allocate an assessment status for the subject patient;

wherein comparing the subject patient dataset to the feature data scheme to allocate the assessment status for the subject patient comprises:

applying the diagnostic model to the subject patient dataset to determine a subject patient diagnosis of one of the known disorders indicated for the subject patient by the subject patient dataset; and selecting and applying one of the diagnosis-specific assessment status models to the subject patient dataset to allocate the assessment status for the subject patient;

and wherein the selected diagnosis-specific assessment status model corresponds to the determined subject patient diagnosis.

45. The medical system of claim 44, wherein the feature data scheme is generated by:

storing, on a system database, a first level training dataset comprising a plurality of records comprising measured patient related data from a large number of patients, the measured patient related data including clinical and/or laboratory data, diagnoses of presence or absence of known disorders and data relating to patient assessment status;

processing the measured patient related data to extract features from the measured patient related data to generate an extracted feature dataset;

processing the extracted feature dataset to derive the feature data scheme;

the feature data scheme including the reduced feature dataset whose cardinality is less than that of the extracted feature dataset;

the reduced feature dataset being derived by processing the data to obtain features appearing to discriminate for a useful prediction.

* * * * *

UNITED STATES PATENT AND TRADEMARK OFFICE
CERTIFICATE OF CORRECTION

PATENT NO.        : 9,460,400 B2
APPLICATION NO.   : 14/182269
DATED             : October 4, 2016
INVENTOR(S)       : Hubert De Bruin et al.

Page 1 of 1

It is certified that error appears in the above-identified patent and that said Letters Patent is hereby corrected as shown below:

In the Claims

In Claim 28 (Column 51, Line 16), "elates" should be "relates".

Signed and Sealed this
Second Day of May, 2017

Michelle K. Lee
*Director of the United States Patent and Trademark Office*